US008571690B2

(12) United States Patent
Bartee et al.

(10) Patent No.: US 8,571,690 B2
(45) Date of Patent: Oct. 29, 2013

(54) NONLINEAR MODEL PREDICTIVE CONTROL OF A BIOFUEL FERMENTATION PROCESS

(75) Inventors: James F. Bartee, Stilesville, IN (US); Maina A. Macharia, Round Rock, TX (US); Patrick D. Noll, Richardson, TX (US); Michael E. Tay, Georgetown, TX (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 687 days.

(21) Appl. No.: 11/927,960

(22) Filed: Oct. 30, 2007

(65) Prior Publication Data

US 2008/0167852 A1 Jul. 10, 2008

Related U.S. Application Data

(60) Provisional application No. 60/917,916, filed on May 14, 2007, provisional application No. 60/863,759, filed on Oct. 31, 2006.

(51) Int. Cl.
*C12M 1/38* (2006.01)
*G05B 13/04* (2006.01)
*C12M 1/36* (2006.01)
*C12M 1/34* (2006.01)
*C12M 1/00* (2006.01)

(52) U.S. Cl.
CPC ............... *C12M 41/48* (2013.01); *C12M 41/12* (2013.01); *C12M 41/44* (2013.01); *C12M 41/46* (2013.01); *C12M 45/09* (2013.01); *G05B 13/04* (2013.01)
USPC ............................... 700/28; 700/299; 703/11

(58) Field of Classification Search
CPC ..................................................... C12M 45/09
USPC ...................................... 700/28, 299; 703/11
See application file for complete search history.

(56) References Cited

U.S. PATENT DOCUMENTS 3,337,414 A * 8/1967 Wilson ............................ 435/95
4,309,254 A * 1/1982 Dahlstrom et al. ............. 203/47
(Continued)

OTHER PUBLICATIONS

Portman, J. et al. Biofuel alternatives to ethanol: pumping the microbial well. Trends in Biotechnology 26, 375-381 (2008).*

(Continued)

*Primary Examiner* — Soren Harward
(74) *Attorney, Agent, or Firm* — Fletcher Yoder P.C.; William R. Walbrun; John M. Miller

(57) ABSTRACT

A system and method are provided for managing batch fermentation in a biofuel production process. A nonlinear control model of yeast growth and fermentable sugar concentration for biofuel (e.g., fuel ethanol) production in a batch fermentation process (pure and/or fed-batch fermentation) of a biofuel production process is provided. Process information for the batch fermentation process is received, and the nonlinear control model executed using the process information as input to determine values of one or more fermentation process variables for the batch fermentation process, e.g., fermentation temperature and/or enzyme flow, for substantially maximizing yeast growth and achieving target fermentable sugar concentrations. The batch fermentation process is then controlled in accordance with the determined values for the one or more fermentation process variables to substantially maximize yeast growth and achieve target fermentable sugar concentrations, where substantially maximizing yeast growth and achieving target fermentable sugar concentrations substantially maximizes biofuel production in the batch fermentation process.

23 Claims, 21 Drawing Sheets

(56) References Cited

U.S. PATENT DOCUMENTS

| | | | |
|---|---|---|---|
| 4,316,956 A * | 2/1982 | Lutzen | 435/96 |
| 4,626,321 A * | 12/1986 | Grethlein et al. | 203/26 |
| 4,744,408 A * | 5/1988 | Pearson et al. | 165/254 |
| 5,036,005 A | 7/1991 | Tedder | |
| 5,134,574 A * | 7/1992 | Beaverstock et al. | 702/84 |
| 5,177,008 A * | 1/1993 | Kampen | 435/139 |
| 5,407,817 A * | 4/1995 | Lightsey et al. | 435/165 |
| 5,477,444 A * | 12/1995 | Bhat et al. | 700/48 |
| 5,555,797 A * | 9/1996 | Chun | 435/286.1 |
| 5,932,456 A * | 8/1999 | Van Draanen et al. | 435/144 |
| 6,510,368 B1 * | 1/2003 | Beardwood et al. | 700/266 |
| 6,569,653 B1 * | 5/2003 | Alard et al. | 435/161 |
| 6,609,119 B1 * | 8/2003 | Meghlaoui | 706/25 |
| 6,792,336 B1 * | 9/2004 | Johnson et al. | 700/266 |
| 6,934,931 B2 | 8/2005 | Plumer et al. | |
| 2002/0077711 A1 | 6/2002 | Nixon et al. | |
| 2003/0040642 A1 | 2/2003 | Goto et al. | |
| 2004/0023349 A1 * | 2/2004 | Bisgaard-Frantzen et al. | 435/161 |
| 2005/0112739 A1 * | 5/2005 | Golubkov | 435/161 |
| 2005/0164355 A1 * | 7/2005 | Vlasenko et al. | 435/101 |
| 2005/0214408 A1 * | 9/2005 | Pilkington et al. | 426/16 |
| 2005/0233030 A1 * | 10/2005 | Lewis et al. | 426/49 |
| 2006/0014260 A1 * | 1/2006 | Fan et al. | 435/161 |
| 2006/0093718 A1 * | 5/2006 | Jurkovich et al. | 426/524 |
| 2006/0225350 A1 | 10/2006 | Spallone et al. | |
| 2006/0281157 A1 * | 12/2006 | Chotani et al. | 435/161 |
| 2007/0078530 A1 * | 4/2007 | Blevins et al. | 700/29 |
| 2007/0089356 A1 * | 4/2007 | Krasutsky et al. | 44/605 |
| 2007/0099282 A1 | 5/2007 | Thompson et al. | |
| 2007/0218541 A1 * | 9/2007 | Denney et al. | 435/267 |
| 2008/0064022 A1 * | 3/2008 | Murthy et al. | 435/286.1 |
| 2008/0103747 A1 | 5/2008 | Macharia et al. | |
| 2008/0103748 A1 | 5/2008 | Axelrud et al. | |
| 2008/0104003 A1 | 5/2008 | Macharia et al. | |
| 2008/0108048 A1 | 5/2008 | Bartee et al. | |
| 2008/0109100 A1 | 5/2008 | Macharia et al. | |
| 2008/0109200 A1 | 5/2008 | Bartee et al. | |

OTHER PUBLICATIONS

Kamm, B. & Kamm, M. Principles of biorefineries. Applied Microbiology and Biotechnology 64, 137-145 (2004).*
Marchetti, J., Miguel, V. & Errazu, A. Possible methods for biodiesel production. Renewable and Sustainable Energy Reviews 11, 1300-1311 (2007).*
Qin, S. A survey of industrial model predictive control technology. Control Engineering Practice 11, 733-764 (2003).*
Teissier, P., Perret, B., Latrille, E., Barillere, J. M. & Corrieu, G. A hybrid recurrent neural network model for yeast production monitoring and control in a wine base medium. Journal of Biotechnology 55, 157-169 (1997).*
Foss, B. A., Johansen, T. A. & Sorensen, A. V. Nonlinear predictive control using local models—applied to a batch fermentation process. Control Engineering Practice 3, 389-396 (1995).*
Ghaly, A. E. & El-Taweel, A. A. Kinetic modelling of continuous production of ethanol from cheese whey. Biomass and Bioenergy 12, 461-472 (1997).*
Han, K. & Levenspiel, O. Extended monod kinetics for substrate, product, and cell inhibition. Biotechnology and Bioengineering 32, 430-447 (1988).*
Johnson, A. The control of fed-batch fermentation processes—a survey. Automatica 23, 691-705 (1987).*
van Uden, N. Temperature profiles of yeasts. In Rose, A. H. & Tempest, D. W. (eds.) Advances in Microbial Physiology, vol. 25, 195-253 (Academic Press, 1984). 2 page excerpt.*
Agrawal, P., Koshy, G. & Ramseier, M. An algorithm for operating a fed-batch fermentor at optimum specific-growth rate. Biotechnol. Bioeng. 33, 115-125 (1989).*

Oh, K.-K., Kim, S.-W., Jeong, Y.-S. & Hong, S.-I. Bioconversion of cellulose into ethanol by nonisothermal simultaneous saccharification and fermentation. Applied Biochemistry and Biotechnology 89, 15-30 (2000).*
South, C. R., Hogsett, D. A. L. & Lynd, L. R. Modeling simultaneous saccharification and fermentation of lignocellulose to ethanol in batch and continuous reactors. Enzyme and Microbial Technology 17, 797-803 (1995).*
Kadam, K. L., Rydholm, E. C. & McMillan, J. D. Development and validation of a kinetic model for enzymatic saccharification of lignocellulosic biomass. Biotechnol Progress 20, 698-705 (2004).*
U.S. Appl. No. 12/052,117, filed Mar. 20, 2008, Stephenson et al.
U.S. Appl. No. 12/052,159, filed Mar. 20, 2008, Stephenson et al.
U.S. Appl. No. 12/165,371, filed Jun. 30, 2008, Macharia et al.
U.S. Appl. No. 12/242,531, filed Sep. 30, 2008, Macharia et al.
U.S. Appl. No. 12/242,568, filed Sep. 30, 2008, Macharia et al.
U.S. Appl. No. 12/242,606, filed Sep. 30, 2008, Macharia et al.
U.S. Appl. No. 12/242,635, filed Sep. 30, 2008, Macharia et al.
De Andres-Toro, B., et al., "Evolutionary Optimization of an Industrial Batch Fermentation Process", European Control Conference, 1997, http://www.cds.caltech.edu/conferences/related/ECC97/proceeds/501_750/ECC615.PDF, 6 pages.
De Andres-Toro, B, J.M Giron-Sierra, J.A. Lopez-Orozco, C. Ferandez-Conde, "Application of genetic algorithms and simulations for the optimization of batch fermentation control", Systems, Man, and Cybernetics, 1997. 'Computational Cybernetics and Simulation'., 1997 IEEE International Conference on Oct. 12-15, 1997, vol. 1, pp. 392-397.
Madar, Janos, Janos Abonyi, Balaz Balasko, Ferenc Szeifert, "Interactive Evolutionary Computation for Model Based Optimization of Batch Fermentation", European Control Conference, 1997, 6 pages.
Xiao, Jie, Ze-Kui Zhou, Guang-Xin Zhang, "Ant colony system algorithm for the optimization of beer fermentation control", Journal of Zhejiang University Science, ISSN 1009-3095, 2004, 5(12): pp. 1597-1603.
Chang, Raymond. "Physical Chemistry for the BioSciences; Chapter 10: Enzyme Kinetics", University Science Books, 2005, pp. 363-400.
Lin, Yan, Shuzo Tanaka, "Ethanol fermentation from biomass resources: current state and prospects", Appl. Microbiol. Biotechnol., 69: 627-642, 2006.
Lee, C.-G., C.H. Kim, S.K. Rhee, "A kinetic model and simulation of starch saccharification and simultaneous ethanol fermentation by amyloglucosidase and *Zymomonas mobilis*", Bioprocess Engineering 7, 1992, 335-341.
"Liquefaction of starch from dry-milled grains", Novozymes, 2004, 5 pages.
De Andres-Toro, B., J.M. Giron-Sierra, P. Fernandez-Blanco, J.A. Lopez-Orozco, E. Besada-Portas, "Multiobjective optimization and multivariable control of the beer fermentation process with the use of evolutionary algorithms", Journal of Zhejiang University Science, ISSN 1009-3095, 2004, 5(4): pp. 378-389.
De Andres-Toro, B., J.M. Giron-Sierra, J.A. Lopez-Orozco, C. Fernandez-Conde, J.M. Peinado, F. Garcia-Ochoa, "A kinetic model for beer production under industrial operational conditions", Mathematics and Computers in Simulation 48, 1998, pp. 65-74.
"Enzyme kinetics and the Michaelis-Menten equation", http://www.le.ac.uk/by/teach/biochemweb/tutorials/michment2print.html, 8 pages.
De Cruz Meleiro, et al.; "Non-Linear Multivariable Predictive Control of an Alcoholic Fermentation Process Using Functional Link Networks;" *Brazilian Archives of Biology and Technology*, vol. 48, No. Special, Jun. 2005; pp. 7-18.
Zoltan Kalman Nagy; "Model based control of a yeast fermentation bioreactor using optimally designed artificial neural networks," *Chemical Engineering Journal*, No. 127; Mar. 1, 2007; pp. 95-109.

* cited by examiner

MV

| | CV Variable | Yeast_1 | Yeast_2 | Yeast_3 | C_Dextrose_1 | C_Dextrose_2 | C_Dextrose_3 |
|---|---|---|---|---|---|---|---|
| | Objective | Desired | Desired | Desired | Desired | Desired | Desired |
| Variable | Objective | | | | | | |
| T_1 | None | ↑↓ | | | | | |
| T_2 | None | | ↑↓ | | | | |
| T_3 | None | | | ↑↓ | | | |
| V_GA_1 | None | ↑ | | | ↑ | | |
| V_GA_2 | None | | ↑ | | | ↑ | |
| V_GA_3 | None | | | ↑ | | | ↑ |
| C_Ethanol_1 | DV (traj) | ↓ | | | ↓ | | |
| C_Ethanol_2 | DV (traj) | | ↓ | | | ↓ | |
| C_Ethanol_3 | DV (traj) | | | ↓ | | | ↓ |
| C_Solids_1 | DV | ↑ | | | ↑ | | |
| C_Solids_2 | DV | | ↑ | | | ↑ | |
| C_Solids_3 | DV | | | ↑ | | | ↑ |
| V_1 | DV (traj) | ↓ | | | ↓ | | |
| V_2 | DV (traj) | | ↓ | | | ↓ | |
| V_3 | DV (traj) | | | ↓ | | | ↓ |

| | CV Variable | T_1 | T_2 | T_3 | V_GA_1 | V_GA_2 | V_GA_3 |
|---|---|---|---|---|---|---|---|
| | Objective | Desired | Desired | Desired | Desired | Desired | Desired |
| Variable | Objective | | | | | | |
| T_1_Cooler | None | ↑ | | | | | |
| T_2_Cooler | None | | ↑ | | | | |
| T_3_Cooler | None | | | ↑ | | | |
| T_Slurry | None | ↑ | ↑ | ↑ | | | |
| F_GA | None | | | | ↑ | ↑ | ↑ |
| F_Slurry | DV | ↑ | ↑ | ↑ | | | |
| H_1_Rx | DV (traj) | ↑ | | | | | |
| H_2_Rx | DV (traj) | | ↑ | | | | |
| H_3_Rx | DV (traj) | | | ↑ | | | |

FIG. 16

NONLINEAR MODEL PREDICTIVE CONTROL OF A BIOFUEL FERMENTATION PROCESS

PRIORITY DATA

This application claims benefit of priority to U.S. Provisional Application Ser. No. 60/917,916 titled "Nonlinear Model Predictive Control of a Biofuel Fermentation Process" filed May 14, 2007, whose inventors were James F. Bartee and Patrick Noll.

This application also claims benefit of priority to U.S. Provisional Application Ser. No. 60/863,759 titled "Model Predictive Control of a Biofuel Production Process" filed Oct. 31, 2006, whose inventors were Michael E. Tay, Maina A. Macharia, Celso Axelrud, and James Bartee.

FIELD OF THE INVENTION

The present invention generally relates to the field of model predictive control of production processes for biofuel and its co-products, and more particularly, to systems and methods for nonlinear model predictive control of a biofuel (e.g., fuel ethanol) fermentation process.

DESCRIPTION OF THE RELATED ART

Biofuel Production Plant

Biofuel refers to any fuel derived from biomass, i.e., from recently living organisms or their bi-products. An exemplary high-level design of a fermentation section of a biofuel production plant or process is shown in FIG. 1, which illustrates how biomass is processed through various processes or stages to produce biofuel and one or more co-products.

As indicated in FIG. 1, biomass, e.g., corn (from a corn source, although any other type of biomass may be used as desired, e.g., other grains, sugarcane, etc.), along with cook water, is provided to a milling and cooking process, including a milling process, a slurry tank, and a cook tank, as shown. In milling, the biomass is broken down to increase the surface area to volume ratio. This increase in surface area allows for sufficient interaction of the fresh water and biomass surface area to achieve a solution of fermentable sugars in water. The mixture, a biomass/water slurry, is then cooked to promote an increase in the amount of biomass-water contact in solution and to increase the separation of carbohydrate biomass from the non-carbohydrate biomass. The output of the milling and cooking units (i.e., the fermentation feed or slurry) is then sent to a fermentation process, where one or more fermentation units (fermentation tanks) operate to ferment the biomass/water slurry produced by the milling and cooking process.

Fermentation is a biological reaction where a living organism (yeast) is used to convert sugar (glucose or dextrose) to biofuel, e.g., ethanol. More specifically, the fermentation process generally utilizes yeast to convert sugars in the slurry or mash to biofuel, e.g., ethanol, and may also utilize various enzymes, such as alpha-amylase (AA), to assist in breaking down corn starch in the slurry to simpler sugars, and glucoamylase (GA), added to the fermentation tank during fill time to further break down sugars to glucose.

Fermentation is typically a fed-batch operation, with a typical fermentation batch time of between 45 and 60 hours. Generally, the fermentation tank is being filled for 20-33% of this time. The mash (a mixture of water and milled corn) is typically pumped to the fermenter at a rate of 200-800 GPM depending on plant size. The mash has generally been treated with alpha-amylase (AA), which, as noted above, is used to assist in breaking down the corn starch to simpler sugars. Yeast is purchased in dry or liquid form and prepared for addition to the fermenter (i.e., fermentation tank) by mixing it with diluted mash in a propagation tank. This yeast mixture is added to the fermenter as it is being filled with mash. As also noted above, another enzyme, glucoamylase (GA), may be added to the fermentation tank during fill time and/or to a pre-fermenter to further break down sugars to glucose. Other ingredients may also be added that are necessary for proper yeast growth, e.g., a nitrogen source, anti-infection source (e.g., antibiotics), and so forth.

As biofuel fermentation is an exothermic process, fermentation tanks are cooled by re-circulating the mash through a heat exchanger whereby it is cooled by an external water source. The temperature of the recycled mash after the cooling heat exchanger may be referred to as the recycle temperature, fermenter cooler return temperature, or simply cooler return temperature, among others.

Note that the system is very sensitive to temperature; the enzymes prefer higher temperatures whereas the yeast prefers lower temperatures. A plant laboratory typically tests several items or constituents of the fermentation material at various times throughout the batch to measure the fermentation process, such as, for example, temperature, pH (measure of acidity), sugars: e.g., DP4 (four chain dextrose polymer), DP3 (three chained dextrose polymer), maltose, glucose, fructose, galactose, lactose, and/or sucrose (and/or others), byproducts: e.g., lactic acid, acetic acid and glycerol, and biofuel, e.g., ethanol.

As FIG. 1 also shows, a yeast propagation process may culture (produce) live yeast for initial inoculation of the mash in the fermentation tanks. The mash is then fermented to produce a mixture of various fermentation products. Note that the fermentation process may or may not require addition of additional fresh water to the process to control the consistency of material to the fermentation units (also referred to herein as a fermenter). In the fermentation units or tanks, biomass is converted by yeast and enzymes into a biofuel, and byproducts such as carbon-dioxide, water and non-fermentable bio-mass (solids).

FIGS. 2 and 3 illustrate typical profiles of various constituents of the fermentation process, including carbohydrates, e.g., sugars, such as DP4, DP3, maltose, fructose, galactose, lactose, and/or sucrose, and biofuel, in these examples, ethanol. As these figures indicate, since the carbohydrates are converted to ethanol, as ethanol concentrations rise, carbohydrate concentrations fall over the course of the fermentation process, i.e., over the batch time or period.

Another aspect of the fermentation process is that over the batch time, the active yeast grows to some maximum, then declines as ethanol concentration increase and the sugars are depleted. FIG. 4 illustrates a calculated rise and eventual decline of the active yeast concentration over the batch time. FIG. 5 illustrates a calculated active yeast profile with respect to ethanol production (both measured and modeled). As may be seen, as the active yeast concentration declines, ethanol production slows, until no further appreciable ethanol is produced.

After fermentation, the output from the fermentation process is sent to a distillation process, e.g., one or more distillation units, to separate biofuel from water, carbon dioxide, and non-fermentable solids. If the biofuel has to be dehydrated to moisture levels less than 5% by volume, the biofuel can be processed through a processing unit called a molecular sieve. The finalized biofuel is then processed to ensure it is denatured and not used for human-consumption.

The distillation units separate the biofuel from water. Fresh water is added in the form of steam for heat and separation, and the condensed water is recycled back to the milling and cooking units, as shown in FIG. 1. Stillage (non-fermentable solids and yeast residue), the heaviest output of the distillation units, is sent to stillage processing for further development of co-products from the biofuel production process.

In prior art biofuels plants, properties such as temperature or product quality are controlled with traditional control schemes. Modern industrial plants apply traditional and advanced controls to regulate complex processes to achieve a specific control objective. Traditional PID (Proportional-Integrated-Derivative) controllers and other control systems such as ratio controls, feed-forward controls, and process models may be used to control biofuel production processes (a PID is a control algorithm or device that uses three basic feedback control modes to act on a deviation from its control objective: proportional action control (P), integral action (I), and derivative (D) rate of change action). A DCS (distributed control system) will have many traditional control schemes set up to control the process unit variables at the local control level.

However, there are numerous aspects of the fermentation process that are not amenable to direct measurement or control, which can result in unreliable or sub-optimal biofuel production. Thus, improved systems and methods for biofuel production are desired.

SUMMARY OF THE INVENTION

Various embodiments of a computer-implemented method for managing a fermentation process of a biofuel production process utilizing model predictive control (MPC) are presented.

First, a nonlinear control model of yeast growth and fermentable sugar concentration for biofuel production in a batch fermentation process of a biofuel production process may be provided. For example, the nonlinear control model of yeast growth and fermentable sugar concentration may be based on, or derived from a fundamental model, as described below, or a variant thereof. Note that as used herein, a control model is an input/output representation of a system or process that determines how much an output changes when an input is changed, and may include instantaneous (steady-state) models as well as dynamic models, as defined below. Control models may be univariate (single input effect a single output) or multivariate (multiple inputs affecting multiple outputs).

Process information for the batch fermentation process may be received, e.g., from the biofuel production process. In various embodiments, this process information may originate from various different sources. For example, the process information may include one or more of: measured properties of the batch fermentation process (e.g., temperature, pressure, water temperature, etc.); property values determined by a laboratory, referred to as laboratory data (e.g., pH; sugar concentrations, such as dextrose (e.g., DP4, DP3), maltose, fructose, galactose, lactose, and/or sucrose; byproducts, such as lactic acid, acetic acid, and glycerol; and biofuel, e.g., ethanol), which may result from testing various parameters at various times throughout the batch; and/or inferred or computed values, e.g., provided by virtual online analyzers.

The nonlinear control model of yeast growth and fermentable sugar concentration may be executed using the process information as input to determine values of one or more fermentation process variables for the batch fermentation process for substantially maximizing yeast growth and achieving target fermentable sugar concentrations. The one or more fermentation process variables preferably include fermentation temperature (i.e., fermenter temperature) and/or enzyme flow, i.e., a rate of enzyme flow to the fermentation process, where, as noted above, the enzyme operates to convert starches to fermentable sugars, e.g., dextrose, maltose, fructose, galactose, lactose, and/or sucrose. Other fermentation process variables may also be included as desired, e.g., pH, additional enzymes, nitrogen source, or any other fermentation process variables.

The batch fermentation process may be controlled in accordance with the determined values for the one or more fermentation process variables to substantially maximize yeast growth and achieve target fermentable sugar concentrations, where substantially maximizing yeast growth and achieving target fermentable sugar concentrations substantially maximizes biofuel production in the batch fermentation process.

BRIEF DESCRIPTION OF THE DRAWINGS

A better understanding of the present invention can be obtained when the following detailed description of the preferred embodiment is considered in conjunction with the following drawings, in which:

FIG. 15 is an exemplary control matrix for the main controller of FIG. 13B, where three fermenters are utilized, according to one embodiment;

FIG. 16 is an exemplary temperature and enzyme concentration sub-control matrix for the sub-controller of FIG. 14, where three fermenters are utilized, according to one embodiment;

Figure 1:
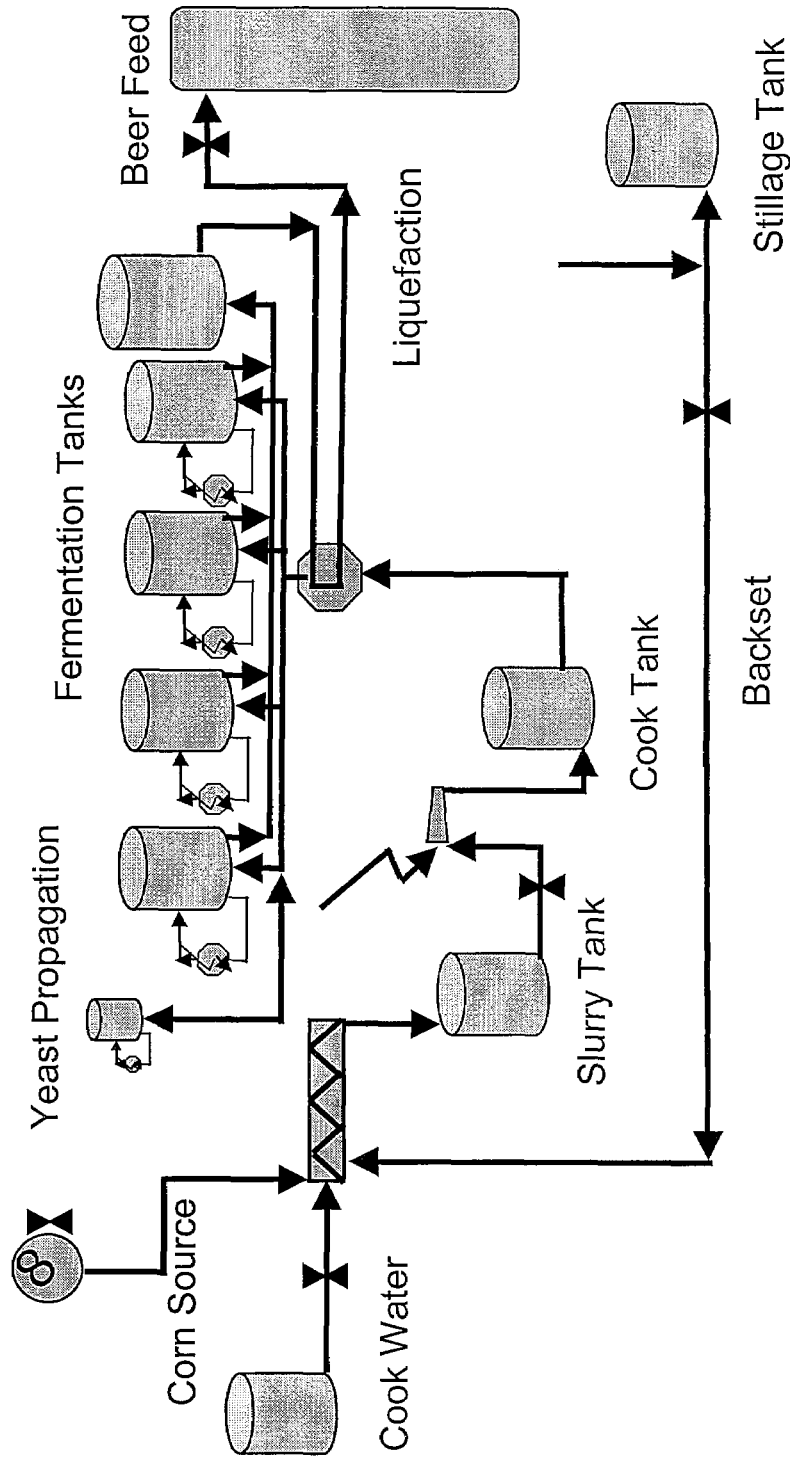
FIG. 1 illustrates a general design of a fermentation section of a biofuel processing plant, according to the prior art.
Figure 2:
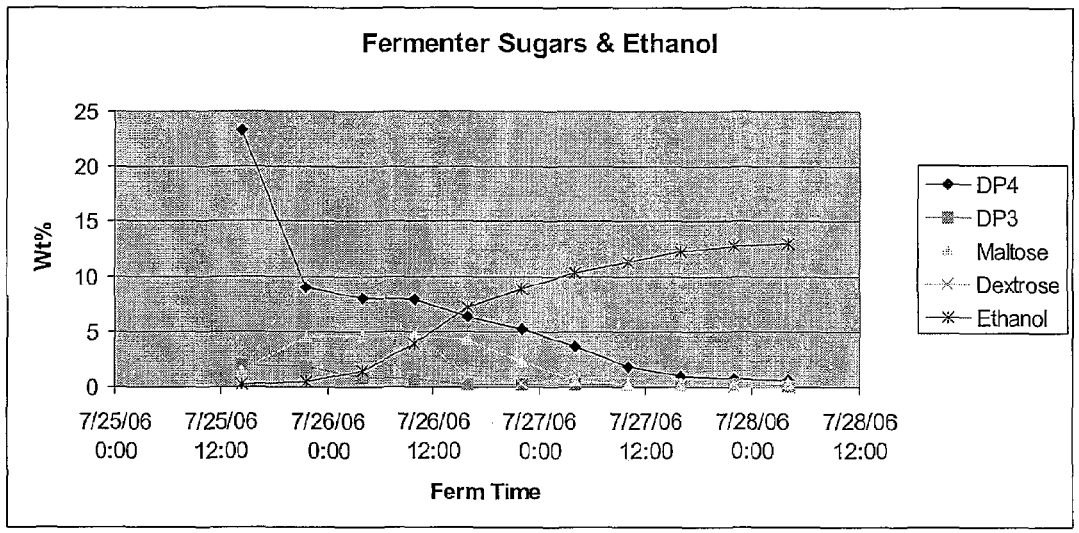
FIGS. 2 and 3 illustrate fermenter sugars and ethanol concentrations over a fermentation period, according to the prior art.
Figure 3:
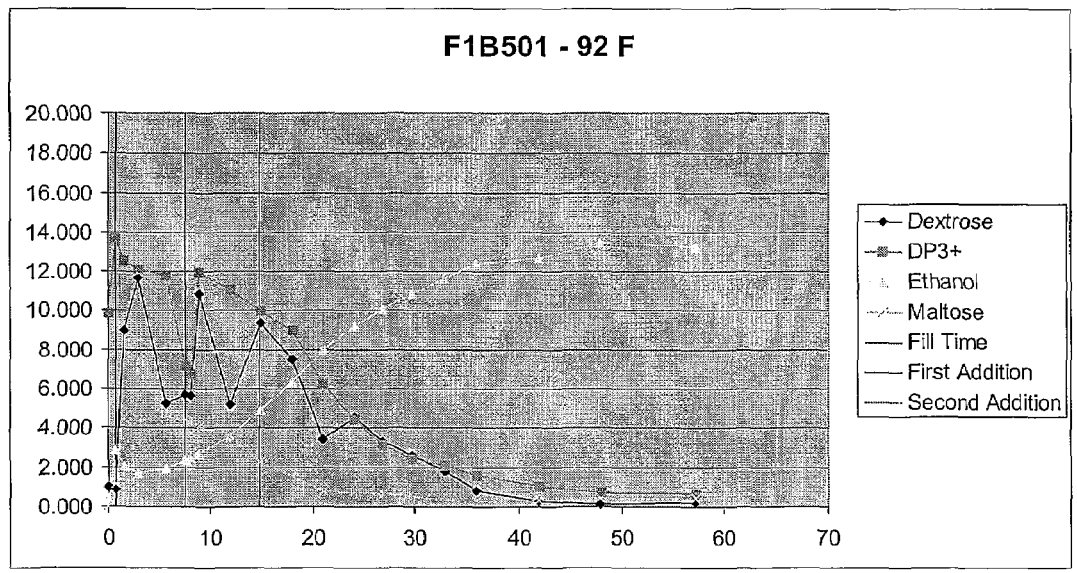

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE INVENTION

Incorporation by Reference

The following references are hereby incorporated by reference in their entirety as though fully and completely set forth herein:

U.S. Provisional Application Ser. No. 60/917,916 titled "Nonlinear Model Predictive Control of a Biofuel Fermentation Process" filed May 14, 2007.

U.S. Provisional Application Ser. No. 60/863,759 titled "Model Predictive Control of a Biofuel Production Process" filed Oct. 31, 2006.

DEFINITIONS

Biofuel Production Processes

Biofuel—any fuel (or fuels) derived from biomass, i.e., from recently living organisms or their bi-products, e.g., fuel ethanol.

Biofuel production process—a fermentation process surrounded by auxiliary processing units to produce biofuel, other fermentable alcohols for fuel, and/or high-capacity food grade or chemical grade alcohols.

Biofuel production—a measure of biofuel production within or at the end of a batch process. May include measurements such as concentration (e.g., wt %, volume % or wt/vol %), volume (e.g., current gallons biofuel within a fermenter) or mass (e.g., current kg biofuel within a fermenter).

Batch processing—a staged discontinuous processing step that includes a start and an end, in contrast to continuous processing that continues without stop, e.g., during a normal operating day or week. Continuous processing is generally represented by fairly steady targets or operations, where at least some parameters change throughout batch processing. For example, biofuel production, e.g., fermentation, starts at low levels at the start of a batch and increases throughout the batch with or without a drop at the end representing degradation rates being higher than production rates. Similarly, yeast cellular concentrations, start at fairly low levels, and generally grow throughout a batch, although they generally have a lag (relatively constant concentrations), exponential growth, stable growth and degradation phase within a batch.

There are typically two kinds of batch fermentation processes: a pure batch process, in which the tank is filled with mash, and when full, is inoculated with yeast and allowed to react; and a fed-batch process, where the fermentation tank is being filled as the reaction progresses, i.e., feed is provided to the tank or vessel after the yeast has been introduced and while the reaction is occurring.

Slurry—a fermentation feed mash comprising a two-phase (liquid and solid) slurry that will be fermented.

Solids or % solids—fraction or percent of solids in the fermentation feed.

Milling and Cooking Process—continuous processing for pre-fermentation of the fermentation feed, which generally includes grain or cane milling, cooking, mixing with water and processing chemicals, cooking for sterilization and increasing water concentration within solids, and other pre-fermentation processing.

Biomass concentration—content attribute of the fermentation feed specified by one or more of: slurry solids, liquefaction solids, slurry density, liquefaction density, slurry % or fraction carbohydrates, and slurry % or fraction fermentable sugar.

Water inventory information—includes water flows, recycle liquid flows, evaporator condensate recycle flow, thin stillage or centrifuge liquor recycle flows, fresh water addition flows, processed water addition flows, slurry flows, mash flows, and various levels or weights for various tanks used to hold inventories of these flows or for intermediate receptacles (e.g. methanator feed tank, slurry feed tank, liquefaction tank, distillate tank, grain silo inventories or other biomass inventories, etc.).

Liquefaction—for grains with high starch content, the starch is liquefied to reduce its carbohydrate chain length and viscosity by adding enzymes or other biologic agents.

Thermal Oxidizer/Heat Recovery Steam Generator (HRSG)—process equipment that is used to destroy volatile organic compounds (VOCs), to reduce air and remove stenches from stillage dryer or evaporation systems. The heat recovery steam generator is used to recover the heat required to destroy the VOCs, and is typically the energy center of the biofuels production process.

Dried Distillers Grains (DDG)—post fermentation solid residue that includes undigested grain residue, other solid residues (enzymes, salts), and yeasts (or other cellular residue) that may be dried and released as a production by-product (generally as animal feed). DDG may also be used herein to include WDG (wet distillers grains), which are only partially dried for local consumption (e.g. without long-term biological stability) and DDGS/WDGS (dried distillers grains with solubles and wet distillers grains with solubles). Solubles includes residue solids that are soluble in water and therefore present in stillage concentrate. Solubles may be partially concentrated (generally with evaporation), and added to DDG or WDG to increase yields and manage by-product inventories.

Enzyme—highly selective biological-based catalyst added to manage specific reactions within a fermentation process. Commonly used enzymes include alpha amylase to rapidly break starches into dextrins, gluco-amylase to break dextrins into glucose, and proteases to break grain proteins into digestible proteins to support cell growth. As described below, modeling and controlling starch-based fermentations, enzymes specific for cellulosic conversion into biofuels or other enzymes affecting yeast growth or nutrient availability may be managed.

Yeast—a biofuel producing organism. Yeasts are currently the most commonly used organism in ethanol production although other biofuel producing organisms including genetically engineered $E.\ coli$ can be substituted throughout as the technology described may not be specific to yeast, and may apply to many organisms used in fermentation processes to produce biofuel.

Active Yeast—refers to yeast as defined above that are actively consuming carbohydrates to produce biofuel. Unless otherwise specified, yeast as referred to in this document is by definition active yeast.

Stillage/Whole Stillage—non-fermentable solids and water liquid removed from the bottom of the primary distillation units.

Thin Stillage—the separated liquid from the stillage non-fermentable solids.

Backset—thin stillage that is recycled back to the fermentation feed line and thus introduced into the fermentation process.

Syrup—concentrated thin-stillage with a large portion of the moisture removed. The % solids in syrup are usually in the range of 20-45% solids, but percentages outside this range may occur.

Fermentation Gap—the cumulative sum of all fermentation tanks as well as the beer well. Represented as volume, % volume, level, % level or like designations.

Beer Well—repository of fermentation tank effluent. Holding tank between the fermentation section and distillation section of many biofuel processes, Azeotrope—a special mixture of two compounds, that when in equilibrium, the vapor phase and liquid phase have exactly the same compositions. This makes it difficult to separate the two components to achieve a better purity. Special separation processes are required to break the azeotrop. They comprise azeotropic distillation (add a $3^{rd}$ compound to break the azeotrop), extractive distillation (use a solvent to separate the 2 compounds), or molecular sieve technology (preferentially trap molecules of one component in a molecular sieve bed as the other component passes over the molecular sieve bed).

Volatile Organic Compounds (VOCS)—Organic compounds that tend to vaporize when subject to atmospheric pressure and ambient temperature ranges.

Capacity—capacity is the established maximum production rate of the process, sub-process, or unit under best operating conditions (no abnormal constraints). Capacity is generally a constant within the present capital investment. For new units it is the vendor's specified capacity. For established units, capacity is established by demonstrated historical production rates.

Model—an input/output representation, which represents the relationships between changes in various model inputs and how the model inputs affect each of the model outputs.

Dynamic Predictive Model/Dynamic Model—an input/output representation of a system or process that not only reflects how much an output changes when an input is changed, but with what velocity and over what time-dependent curve an output will change based on one or more input variable changes. A dynamic multivariate predictive model is a dynamic predictive model that represents or encodes relationships among multiple parameters, and is operable to receive multiple inputs, and generate multiple outputs.

Control Model—an input/output representation of a system or process that determines how much an output changes when an input is changed, and may include instantaneous (steady-state) models as well as dynamic models, as defined above. Control models may be univariate (single input effect a single output) or multivariate (multiple inputs effecting multiple outputs).

Model Predictive Control (or MPC)—use of multivariate dynamic process models to relate controller objectives (targeted controller outputs and constraints) with regulatory controllers (existing single-input/single-output controllers such as ratio flow, temperature, level, speed, or pressure controllers) over a predicted time interval (e.g., 1 minute, 30 minutes, 2 hours, 100 hours, etc.).

Objective Function—the objective function encodes an objective that sets the goal or goals for the overall operation of the process, sub-process, or unit. The objective function provides one or more consistent numerical metric(s) to which the process, sub-process, or unit strives to achieve and over which the performance of the process, sub-process, or unit may be measured, e.g., from a business standpoint e.g., to minimize the cost of operation, or maximize profit or production of the operation.

Control Variables—(also called controlled variables) those variables that the controller/optimizer tries to bring to some objective, e.g., to a target value, maximum, etc.

Integrated Variables—integrated control variables are variables that are not stable, but integrate generally with a stable first derivative as a function of time. The most common integrated variable is a tank level where as long as inputs and outputs are imbalanced the level will increase or decrease. Thus, when balanced a change in an input or output flow will cause a tank to either overfill or drain as integrated over time. A controller must use these integration calculations to determine when and how rapidly input or output flows must be adjusted.

Manipulated Variables—those variables over which the management of the process or unit has authority and control, e.g., via regulation of the process with online controllers, and which are changed (moved), or manipulated by the controller/optimizer to achieve the targets or goals of the control variables. These variables are the actual control variables whose values are limited by the constraints. This is in distinction from controllable constraints in the sense that manipulated variables may operate within some range of controllable or fixed constraints. Manage is an alternate term for process control.

Disturbance Variable—a variable representing an external influence on a process that, in addition to objective variables and regulatory controllers, is outside the controller scope, and so it acts on the objective variables, but independently of the described controller. Disturbance variables are used in feed-forward disturbance rejection. Disturbance variables are also measured or unmeasured variables over which the management of the process or unit does not have direct authority or control. For example, temperature, humidity, upstream flow, or quality, may all be referred to as measured disturbance variables.

Set Point (target)—the target signal or value for a manipulated variable or targeted controlled variable.

Constraints—Constraints represent limitations on particular operating variables or conditions that affect the achievable production rate of a production unit. Constraints are of two types: controllable and external, defined below. Constraints may include, but are not limited to: safety constraints, equipment constraints, equipment availability constraints, personnel constraints, business execution constraints, control constraints, supply chain constraints, environmental permit and legal constraints. Safety constraints ensure the safety of equipment and personnel. Equipment constraints, such as the maximum open position of a control valve, maximum tank capacity, etc., may limit the physical throughput of the unit. Equipment availability constraints may include, but are not limited to: readiness due to maintenance planning and scheduling, or due to unexpected equipment outages, authorized production level set by the supply chain and production scheduling systems. Personnel constraints refer to limitations on the availability of staffing and support functions, business rules and constraints imposed by contract and policy. Business execution constraints are limits imposed by the time required to execute associated business and contractual tasks and obligations. Control constraints are limits on the maximal position and rate of change of manipulated variables. Supply chain constraints are limits on the availability of raw materials, energy, and production supplies. Environmental permit and legal constraints are limits on air emissions, waste water, and waste disposal systems, and/or environmental constraints imposed upon the performance of the unit, such as river levels and current weather imposed limitations.

Controllable Constraints—constraints imposed on the performance of a process or unit over which the management of the process or unit does have authority and discretionary control. For example, the separation in a distillation tower may be affected by distillation tray fouling. The tray fouling is a function of how the feed-stock is processed, and how often the unit is taken offline for clean-up. It is management's discretion as to when the unit is serviced. Controllable constraints change a unit's throughput capacity.

External Constraints—external constraints are limitations imposed on the performance of the process, sub-process, or unit over which the management of the process, sub-process, or unit does not have authority or discretionary control. These external constraints come in two types: external constraints that are controllable by other entities or processes in the plant or in the supply chain, and those constraints that are imposed by physical, safety, environmental, or legal constraints and are not controllable by anyone in the plant or supply chain.

System—a system may be defined by the inputs and the characteristics of the system or process. In the biofuel production process, the system may be defined as: the entire biofuel production process, a sub-process of the biofuel production process such as the milling and cooking process, or a variable in a sub-process such as the cooking temperature.

Open Loop Systems—systems that respond to an input, but where the system is not modified because of the behavior of the output. For example, in a biofuel system, a reciprocating pump will operate and move at a fixed volume of syrup independent of the upstream and downstream pressure if the reciprocating pump does not have a pressure control system.

Closed Loop Systems—systems in which system inputs may be adjusted to compensate for changes in the output. These changes may be a deviation from an objective for the system, impacts of constraints on the system or system variables, or measurements of output variables. The closed loop system may be used to sense the change and feedback the signal to the process input. In biofuel systems, closed loop systems may predominate, since these systems may be regulated subject to constraints such as production (product) quality, energy costs, process unit capacity, etc.

Control System—the regulatory level mechanism by which the manipulated variables are driven to the set points.

Response—the measurement of the current position of the manipulated variable. The response is the feedback of the movement of the manipulated variable to the set point in response to the actions of the control system in its effort to achieve the set point.

Target Profile or Trajectory—a desired profile or trajectory of variable values, i.e., a desired behavior of a control variable or a manipulated variable, e.g., over a specified period of time, e.g., over a horizon.

Control Horizon—the period of the time extending from the present into the future during which one plans to move or change manipulated variables. Beyond this horizon the MV is assumed to stay constant at its last or most recent value in the control horizon.

Prediction Horizon—the period of time extending from the present into the future during which the process or system response is monitored and compared to a desired behavior.

Cloning—the process of exercising a fundamental model over a desired range of inputs and outputs and using the results to create a neural network model.

MPC Applied to Fermentation in a Biofuel Production Process

Below are described various embodiments of systems and methods for applying model predictive control to fermentation in a biofuel production process. More specifically, new insights regarding the relationships between yeast growth, fermentable sugar (e.g., dextrose) concentrations, and biofuel (e.g., ethanol) production are used to substantially maximize biofuel production indirectly by controlling yeast growth, as will be described below in detail. It should be noted that while the techniques disclosed herein are contemplated as applicable to biofuel production in general, the following embodiments are described in terms of ethanol production; however, this is not meant to limit the invention to any particular biofuel.

As noted above, the fermentation process uses a living organism (e.g., yeast) to convert fermentable sugar (e.g., dextrose, maltose, fructose, galactose, lactose, and/or sucrose) to biofuel, e.g., fuel ethanol, butanol, and/or methanol) with a by-product of carbon dioxide and energy. While there are several products of the fermentation process, in preferred embodiments, the main product (and the product of interest) is the production of biofuel, e.g., fuel ethanol (and/or butanol and/or methanol). Other components, such as the acids, while normally produced in small quantities, can indicate a problem within the fermenter if produced in larger amounts. A key point of the process according to embodiments of the present invention is that not only is the yeast present, but it is reproducing ("active"). Active yeast has the greatest capacity for producing ethanol. Three main factors in yeast growth are the fermenter temperature, the concentration of fermentable sugars (e.g., dextrose) and the concentration of ethanol. This is illustrated conceptually by the following equation:

$$\frac{dy_{active}}{dt} = f(T, y_{sugar}, y_{EtOH}) y_{active} + Yeast_{initial} \qquad (1)$$

where:

$y_{active}$=active yeast concentration, $y_{sugar}$=fermentable sugar (dextrose) concentration, $Y_{EtOH}$=ethanol concentration, T=fermenter temperature, and $Yeast_{initial}$=initial inoculation of yeast Note that, unlike a typical chemical reaction model, this expression is a growth model for the yeast. Note also that this expression is provided for illustrative purposes only; a detailed kinetic model, including the effect of dilution, is described below. Yeast will grow and die with rates based on conditions in the fermenter. As discussed above with reference to FIG. 1, the initial inoculation of yeast is introduced into the fermenter from the yeast propagation tank. It typically takes about an hour to empty the yeast propagation tank. Therefore, for the majority of the batch, the yeast growth is given by:

$$\frac{dy_{active}}{dt} = f(T, y_{sugar}, y_{EtOH}) y_{active} \qquad (2)$$

This exemplary expression illustrates the fact that once the initial inoculation is complete, the yeast growth is relatively independent of the inoculation, but is dependent on temperature, sugar concentration, and ethanol concentration.

Figure 4:
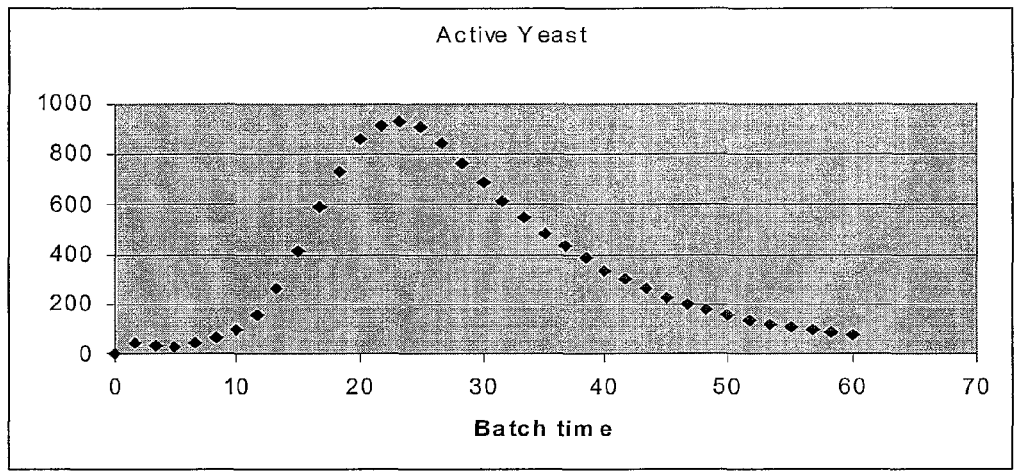
FIG. 4 illustrates calculated active yeast concentration over a fermentation period, according to one embodiment.

Referring back to FIG. 4, described above, a typical yeast profile is illustrated, showing the rapid growth, peak, and subsequent decline of yeast concentration. There are a several notable aspects the equation (2) (as illustrated in FIG. 4). First, there is no steady state value, or, more correctly, the steady state value is zero. In other words, the yeast will continue to grow (a linearly unstable system) or will die off (a linearly stable system tending toward zero) depending on the value of the function ($f(T, y_{sugar}, y_{EtOH})$ in equation (2)). This function is referred to herein as the yeast growth function.

Active yeast is the main driver for the ethanol production, which can be represented by a nonlinear integrating function:

$$\frac{dy_{EtOH}}{dt} = g(T, y_{sugar}, y_{EtOH}) y_{active} \qquad (3)$$

Figure 5:
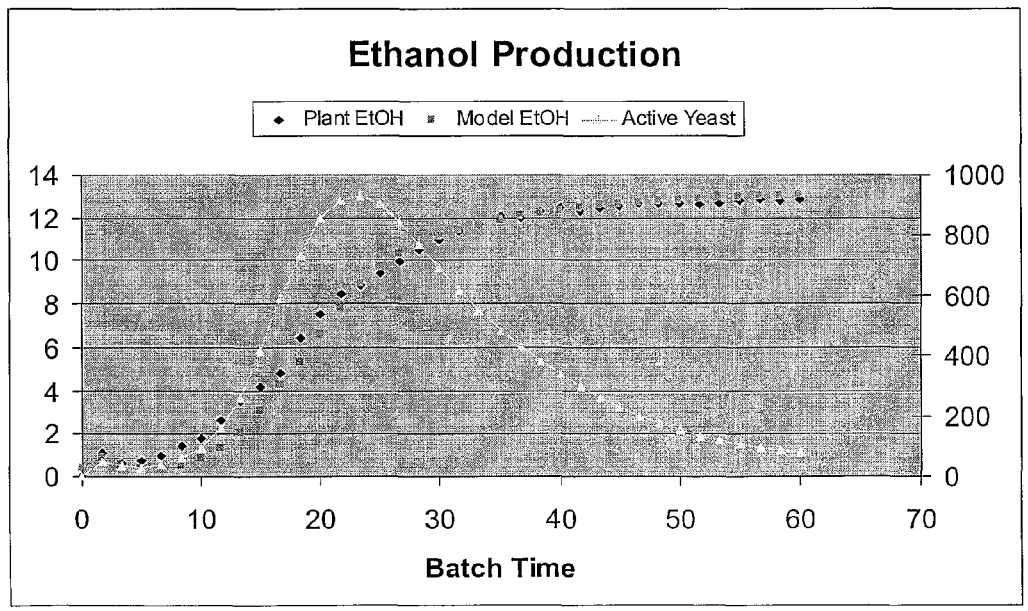
FIG. 5 illustrates calculated ethanol production and active yeast concentration over a fermentation period, according to one embodiment.

This relationship is illustrated in FIG. 5, discussed above, which plots typical ethanol production and yeast concentration in a fuel ethanol fermentation unit. Note that since the production of ethanol behaves as an integrated function of the yeast growth, maximization of the active yeast may therefore maximize the amount of produced ethanol. Thus, maximization of the yeast growth function may ensure the substantially maximum amount of active yeast in the fermentation unit at any given time. Based on this observation, the production of ethanol in an industrial fuel ethanol fermentation process can be controlled implicitly by controlling the growth of the yeast, where yeast growth is defined by the yeast growth function, which in one embodiment is given by:

$$\text{yeast growth function} = \left( \frac{\mu_x^{max}(T) y_{sugar}}{(k_{x1} + y_{EtOH})(k_{x2} + y_{sugar})} - r_d(T) \right) \qquad (4)$$

This expression is described below in more detail. It should be noted that this model of biological organism growth is meant to be exemplary, and that in other embodiments, other models may be used as desired.

Kinetic Model for Fuel Ethanol Fermentation

In many cases, there may be aspects or attributes of the fermentation process that are not readily available, e.g., that cannot be measured, but that may be needed for model predictive control of the process. Thus, due to this lack of control appropriate measurements, a fundamental (i.e., physics based) model may be developed or otherwise provided that takes into account key components of the fermentation process, including for example: mash flow to fermenter, addition of yeast from propagation tank, addition of glucoamylase enzyme, yeast growth, glucose creation and depletion, starch depletion (sugar source—dextrin), ethanol production, and fermentation temperature, among others. Note that these parameters are meant to be exemplary only, and that any other parameters may be used as desired.

In various embodiments, the fundamental model may include mass and/or energy balance relationships, and may also include a kinetic model, described below. As is well known, kinetic models express relationships between production and reactant concentrations. The following describes one embodiment of the kinetic model, which is the first fundamental model that accurately reflects the behavior of a fuel ethanol fermentation process as operated in standard industry. Note that the following model is meant to be exemplary only, and that other variations may be used as desired. For example, in the embodiment described, the model includes a plurality of equations directed to various aspects of the fermentation process, although in other embodiments, different aspects may be modeled as desired.

A. Volumetric Change in Fermentation Tank $$\frac{dV}{dt} = F_{slurry} + F_{Prop} \qquad (5)$$

$F_{slurry} = 0$ when $V = V_{Full}$, $F_{Prop} = 0$ when $V_{Prop} = 0$ where:

V=volume of fermenter, $F_{slurry}$=flow of mash slurry, and $F_{Prop}$=flow from propagation tank.

B. Activation of Yeast $$\frac{dy_{Lag}}{dt} = \left( -\mu_{Lag} - \frac{F_{slurry} + F_{Prop}}{V} \right) y_{Lag} + \frac{F_{Prop}}{V} Yeast_{Prop} \qquad (6)$$

where:

$\mu_{Lag}$=conversion rate, $y_{lag}$=concentration of lag yeast (yeast not yet active), and $Yeast_{prop}$=amount of yeast in propagation tank.

C. Growth of Yeast $$\frac{dy_{active}}{dt} = \left( \mu_x - r_d - \frac{F_{slurry} + F_{Prop}}{V} \right) y_{active} + \mu_{lag} y_{lag} \qquad (7)$$

where:

$$\mu_x = \text{growth rate} = \frac{\mu_x^{max} y_{sugar}}{(k_{x1} + y_{EtOH})(k_{x2} + y_{sugar})},$$

$\mu_x^{max}$=theoretical maximum growth rate=$f(T)$,
$k_{x1}$=Ethanol saturation constant,
$k_{x2}$=dextrose saturation constant,
$r_d$=death rate=$f(T)$, and
$y_{active}$=concentration of active yeast.

D. Death of Yeast $$\frac{dy_{dead}}{dt} = r_d y_{active} - \frac{F_{slurry} + F_{Prop}}{V} y_{dead} \quad (8)$$

where:
$r_d$=death rate=$f(T)$, and
$y_{dead}$=concentration of dead yeast.

E. Conversion of Sugars $$\frac{dy_{sugar}}{dt} = r_{GA} y_{Dex} - \mu_s y_{active} - \frac{F_{slurry} + F_{Prop}}{V} y_{sugar} + \frac{F_{slurry}}{V} Sugar_{Feed} \frac{F_{Prop}}{V} Sugar_{Prop} \quad (9)$$

where:
$r_{GA}$=conversion of dextrins to glucose by $$\text{Glucoamylase} = \frac{\mu_{GA}^{max} y_{GA}}{k_{GA} + y_{Dex}},$$

$\mu_{GA}^{max}$=theoretical maximum growth rate=$f(T)$, $$\mu_s = \text{conversion rate} = \frac{\mu_s^{max} y_{sugar}}{k_s + y_{sugar}}$$

(Michaelis-Menten function, Monad kinetics),
$\mu_s^{max}$=theoretical maximum growth rate=$f(T)$,
$k_s$=saturation constant,
$y_{sugar}$=concentration of convertible sugar (glucose/dextrose),
$Sugar_{Feed}$=fermentable sugars in mash feed, and
$Sugar_{Prop}$=fermentable sugars in propagation tank at drop.

F. Production of Ethanol $$\frac{dy_{EtOH}}{dt} = \mu_a f_a y_{active} - \frac{F_{slurry} + F_{Prop}}{V} y_{EtOH} + \frac{F_{Prop}}{V} EtOH_{Prop} + \frac{F_{Feed}}{V} EtOH_{Feed} \quad (10)$$

where:

$$\mu_a = \text{conversion rate} = \frac{\mu_a^{max} y_{sugar}}{k_s + y_{sugar}}$$

(Michaelis-Menten function, Monad kinetics),
$\mu_a^{max}$=theoretical maximum growth rate=$f(T)$,
$k_s$=saturation constant,
$f_a$=inhibition factor=$(1-\alpha y_{EtOH})$,
$ETOH_{Prop}$=Ethanol in propagation tank,
$ETOH_{Feed}$=Ethanol in Feed Mash, and
$y_{EtOH}$=concentration of ethanol.

G. Dextrin Conversion $$\frac{dy_{Dex}}{dt} = \frac{F_{slurry}}{V} y_{Dex}^{IN} - \frac{F_{slurry} + F_{Prop}}{V} y_{Dex} - r_{GA} y_{dex} \quad (11)$$

where:
$y_{Dex}^{IN}$=sugar concentration in feed stream,
$r_{GA}$=conversion rate of dextrins to glucose by $$\text{Glucoamylase} = \frac{\mu_{GA}^{max} y_{GA}}{k_{GA} + y_{Dex}},$$

and
$y_{Dex}$=concentration of Dextrin (longer chain sugars—DP2, DP3, etc. . . . ).

H. Enzyme Addition
Shot Tank Approach $$y_{GA} = \frac{GA_1}{V} \delta(t - t_{PropDrop}) + \frac{GA_2}{V} \delta(V - \beta V_{full}) \quad (12)$$

where:
$y_{GA}$=concentration of glucoamylase,
$GA_1$=volume of first addition of glucoamylase,
$GA_2$=volume of second addition of glucoamylase, and
$\beta$=fraction total ferm volume for second addition.
Note: this can be expanded to any number of enzyme additions.

Continuous Enzyme Feed $$\frac{dy_{GA}}{dt} = \frac{F_{GA}}{V} - \left(\frac{F_{slurry} - F_{Prop}}{V}\right) y_{GA} \quad (13)$$

where:
$y_{GA}$=concentration of glucoamylase, and
$F_{GA}$=enzyme flow.

I. Yeast Growth Function

Figure 6:
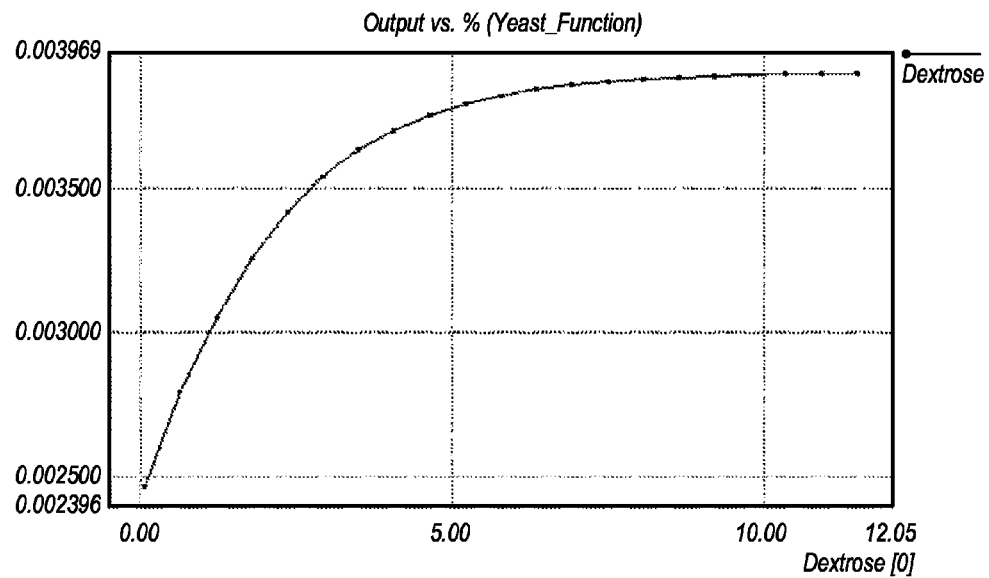
FIG. 6 illustrates the effect of fermentable sugars (dextrose) on yeast growth, according to one embodiment.

Careful study of plant data taken over a period of time as resulted in the following observation and conclusion: The yeast growth function is affected by fermentable sugars only to a substantially maximum concentration. In contrast to published work on yeast growth, a maximum concentration for the fermentable sugars for which the yeast growth will increase has been determined by calculating cause and effect relationships from plant data. FIG. 6 illustrates the effect of fermentable sugars (e.g., dextrose) on yeast growth, where the dextrose is represented in wt %/volume (i.e., concentration). As may be seen, as dextrose concentration increases, yeast growth increases rapidly, then slows, approaching a maximum value. This relationship is represented in one embodiment of the model via the yeast growth rate, which is the positive portion of the yeast growth function:

$$\mu_x = \text{yeast growth rate} = \frac{\mu_x^{max}(T) y_{sugar}}{(k_{x1} + y_{EtOH})(k_{x2} + y_{sugar})} \quad (14)$$

Note that the function illustrated in FIG. 6 represents the output of a neural network trained on plant data consisting of ethanol concentration, dextrose concentration, temperature and active yeast concentration. From the active yeast equation, the yeast growth function is given by the following.

$$f(T, y_{sugar}, y_{EtOH}) = \frac{d y_{active}}{dt}\left(\frac{1}{y_{active}}\right) + \frac{F_{mash}}{V} \quad (15)$$

Note that this is a state-dependent function representing the growth rate of the active yeast in the fermenter. The yeast growth may be estimated by taking a simple energy balance around the fermentation process and approximating the active yeast concentration as proportional to the heat of reaction, as expressed in the following equation:

$$y_{active} = \alpha \Delta H_{R \times N} \quad (16)$$

Figure 7:
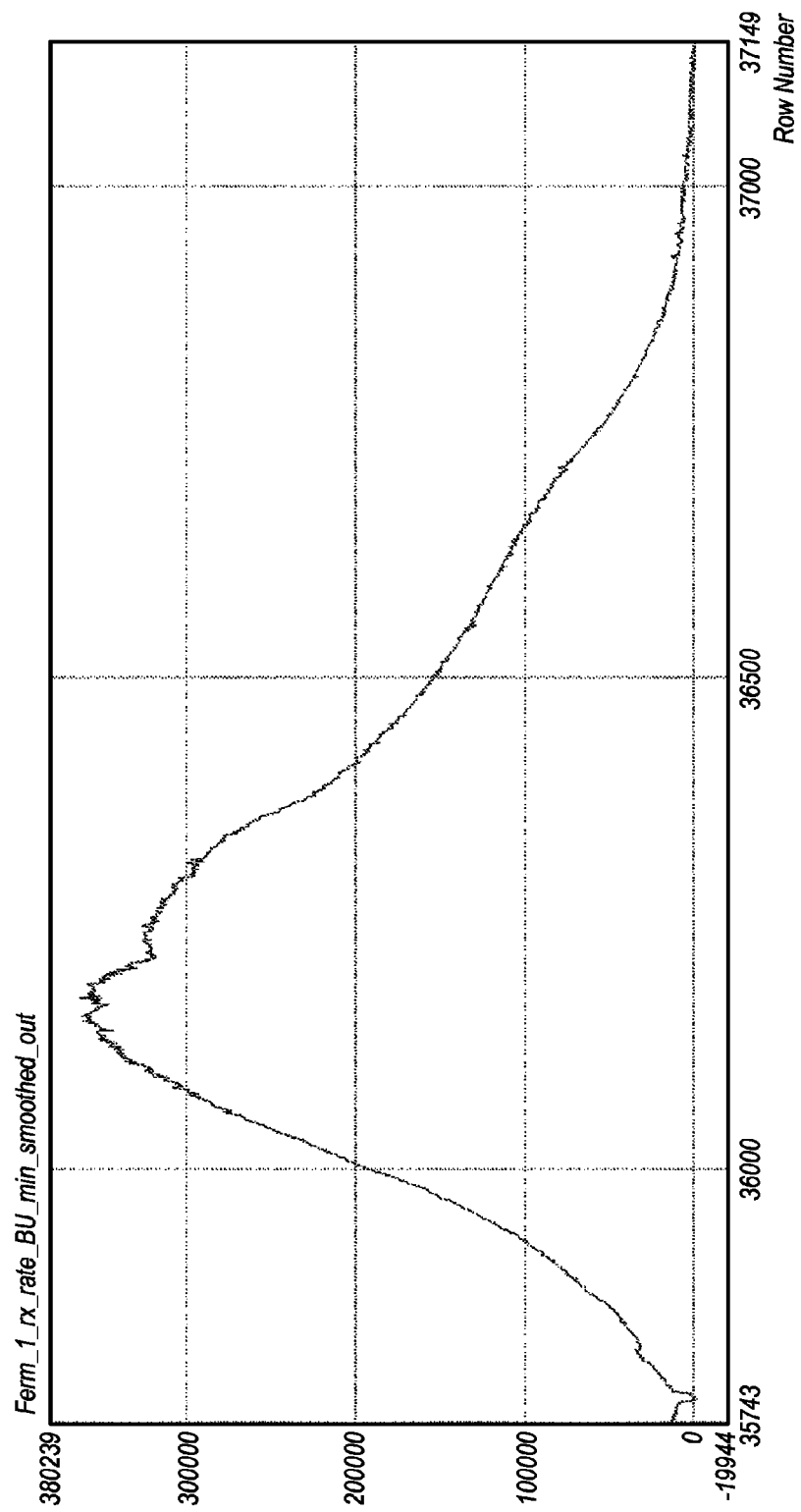
FIG. 7 illustrates energy balance for the fermentation process, according to one embodiment.

FIG. 7 illustrates the heat of reaction (the Y-axis in BTU/min) with respect to time (the X-axis in minutes). Notice the similarities to FIG. 4 above, i.e., the heat of reaction roughly tracks the growth of the yeast.

Temperature Dependence of Fuel Ethanol Production

The kinetic model presented above defines a relationship of fermentation process inputs to ethanol production for a given batch time. An optimal fermentation temperature may exist that provides conditions for substantially maximum yeast growth throughout the operation of the batch process. This optimal temperature may be determined from the fundamental kinetic model described above. More specifically, the optimal fermentation temperature may be determined by substantially maximizing the yeast growth function.

Figure 8:
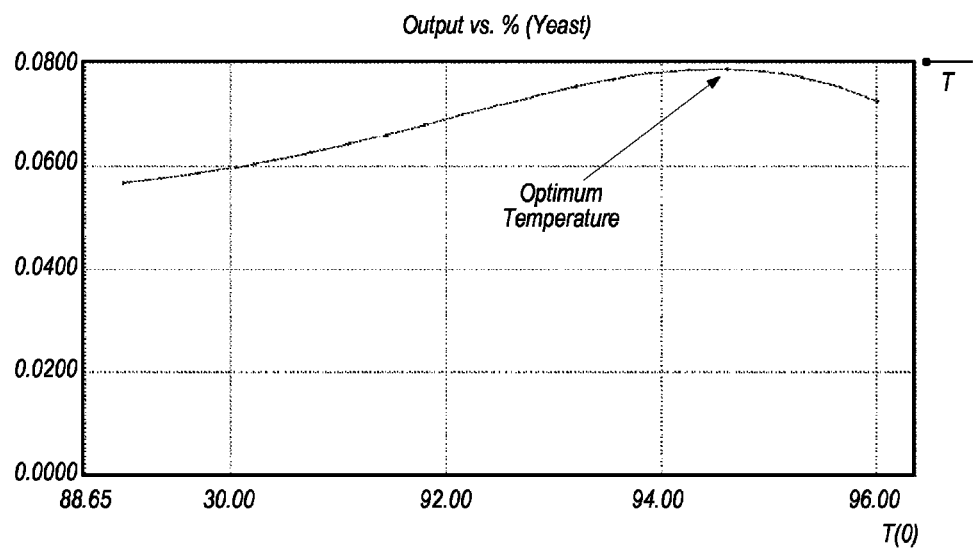
FIGS. 8 through 10 illustrate the effect of temperature on yeast growth at various ethanol concentrations, according to one embodiment.
Figure 9:
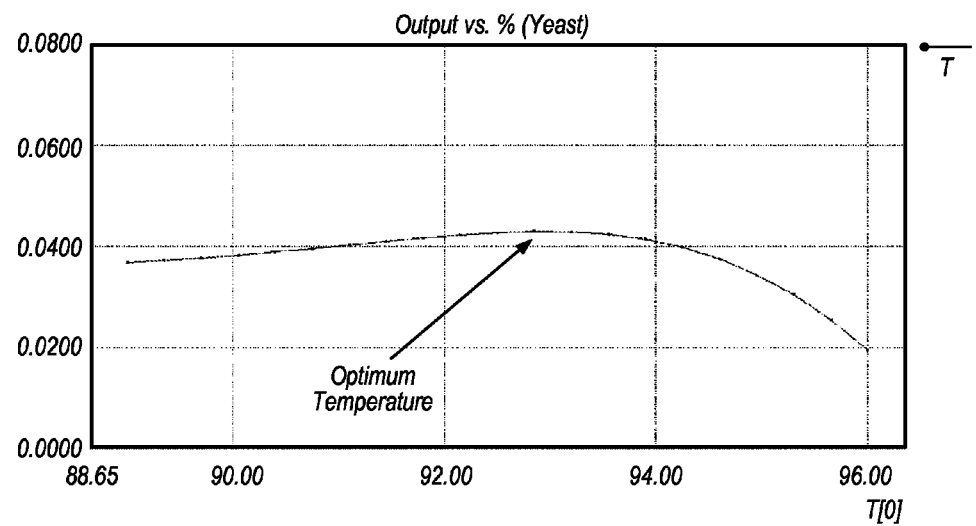
Figure 10:
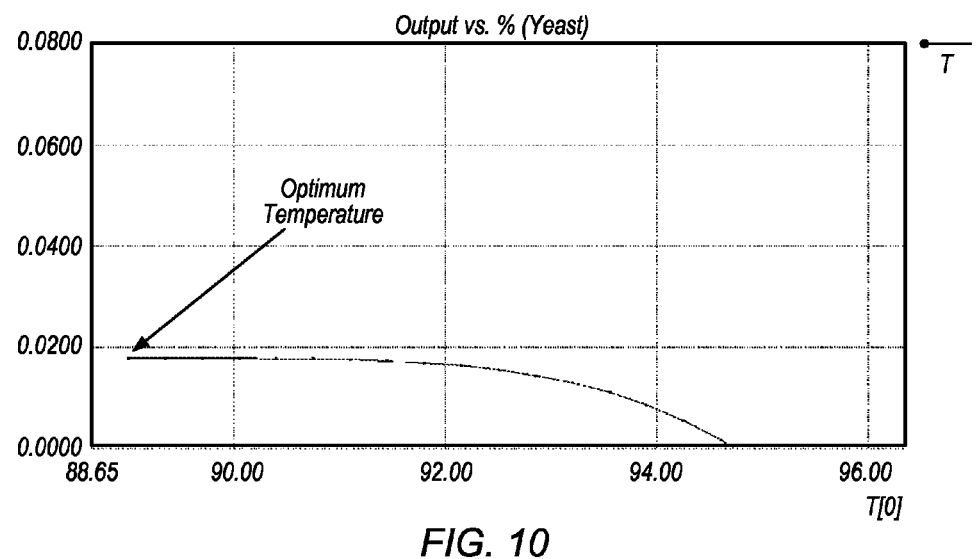

The relationships between temperature and ethanol production is illustrated by FIGS. 8-10, which illustrate the effect of temperature on yeast growth function at a respective ethanol concentration, according to one embodiment. It should be noted that the relationships illustrated in these figures is also germane to various other biofuel processes where biofuel is derived from micro-organisms. In other words, for other such biological processes, the general function of organism growth related to biofuel production corresponds specifically to a function of yeast growth related to ethanol production).

For example, FIG. 8 illustrates the effect of temperature on yeast growth function at a respective ethanol concentration of 3.0 wt %/volume of ethanol. As may be seen, in this example, the optimal temperature for substantially maximizing yeast growth is between 94 and 96 degrees. FIG. 9 illustrates the effect of temperature on yeast growth function at a respective ethanol concentration of 3.6 wt %/volume of ethanol, where, as may be seen, the optimal temperature for substantially maximizing yeast growth is approximately 93 degrees. FIG. 10 illustrates the effect of temperature on yeast growth function at a respective ethanol concentration of 4.5 wt %/volume of ethanol, where, as shown, the optimal temperature for substantially maximizing yeast growth is approximately 88 degrees. Thus, yeast growth may be substantially maximized via control of fermentation temperature.

Nonlinear Model Predictive Control of the Fermentation Process

Based on the above considerations, ethanol (or other biofuel) production may be substantially maximized by substantially maximizing yeast growth (i.e., by substantially maximizing the yeast growth function) and controlling the amount of fermentable sugars (e.g., dextrose) in the fermentation unit. According to embodiments of the present invention, this may be accomplished using a nonlinear model predictive control approach. Note that as used herein, the term "nonlinear model" is also intended to include linear models; i.e., linear models are a subset of nonlinear models. Note also that in some embodiments, the batch fermentation process may be or include a fed-batch fermentation process. As is well-known in the fermenting arts, a pure batch process is one where the tank is filled with mash, and then when full, inoculated with yeast and allowed to react. This is in contrast to a fed-batch process, where the fermentation tank is being filled as the reaction progresses. In other words, feed is provided to the tank or vessel after the yeast has been introduced and while the reaction is occurring. Thus, in various embodiments, the batch fermentation process may be a pure batch or fed-batch process.

Note that the fermentation process utilizes one or more fermenters (also referred to as fermentation units). As described above, the one or more fermenters may receive a fermentation feed, a mixture of liquids and biomass solids, from the milling and cooking units, and may batch process the fermentation feed through a staged temperature profile with the addition of yeast and enzymes to the fermenting mash to produce a combination of biofuel and stillage that may be output to distillation units. The distillation process outputs a stillage slurry to the stillage process units, where the slurry may be separated into a thin stillage (liquids) and solid stillage. Part of the thin-stillage may be recycled back to the fermentation process and added directly to the fermenters, or the thin stillage may be added to the fermentation feed. This is referred to as backset. The fermenters may be operated in staggered cycles so that each fermenter completes a fermentation cycle at a different time, to provide an approximate of continuous output flow to accumulation holding tanks and then on to the distillation units.

Below are described various systems and methods for using model predictive control to improve the yield, throughput, and/or energy efficiency of a biomass batch fermentation process in accordance with specified objectives. These objectives may be set and various stages of the batch fermentation process may be controlled to provide real-time control of the production process. The control actions may be subject to or limited by plant and external constraints. More specifically, in various embodiments of the invention, a dynamic nonlinear control model (or models) and controller(s) may be utilized in a biofuel production plant to control one or more aspects of the fermentation process, including, but not limited to, temperature of the fermenting biomass, and amount and timing of the addition of enzymes to the fermenters, i.e., enzyme flow, among other process variables.

Any of the operations and controllable variables of the fermentation process may be managed or controlled in a biofuel production plant using model predictive control techniques applied throughout a batch fermentation process to maintain, optimize, or substantially maximize targeted amounts of fermented biofuel. Below are described various exemplary systems and methods for doing so, although it should be noted that the particular operations and variables discussed are meant to be exemplary, and that other aspects of the fermentation process may also be managed using model predictive control as desired. Model predictive control techniques may also be applied to the preparation of a continuous fermentation slurry feed to multiple parallel batch fermenters, and to the purification of a continuous output product stream from a set of parallel fermenters by a continuous distillation process. The continuous output product stream may be provided to the distillation process by staggering the process ending times for the batch process in each fermentor, so that each fermenter in a parallel set of fermentors finishes its batch process at a different time.

It should be noted that as used herein, the terms "maximum", "minimum", "optimal", and "optimum", may refer respectively to "substantially maximum", "substantially minimum", "substantially optimal", and "substantially optimum", where "substantially" indicates a value that is within some acceptable tolerance of the theoretical extremum, optimum, or target value. For example, in one embodiment, "substantially" may indicate a value within 10% of the theoretical value. In another embodiment, "substantially" may indicate a value within 5% of the theoretical value. In a further embodiment, "substantially" may indicate a value within 2% of the theoretical value. In yet another embodiment, "substantially" may indicate a value within 1% of the theoretical value. In other words, in all actual cases (non-theoretical), there are physical limitations of the final and intermediate control element, dynamic limitations to the acceptable time frequency for stable control, or fundamental limitations based on currently understood chemical and physical relationships. Within these limitations the control system will generally attempt to achieve optimum operation, i.e., operate at a targeted value or constraint (max or min) as closely as possible.

Figure 11:
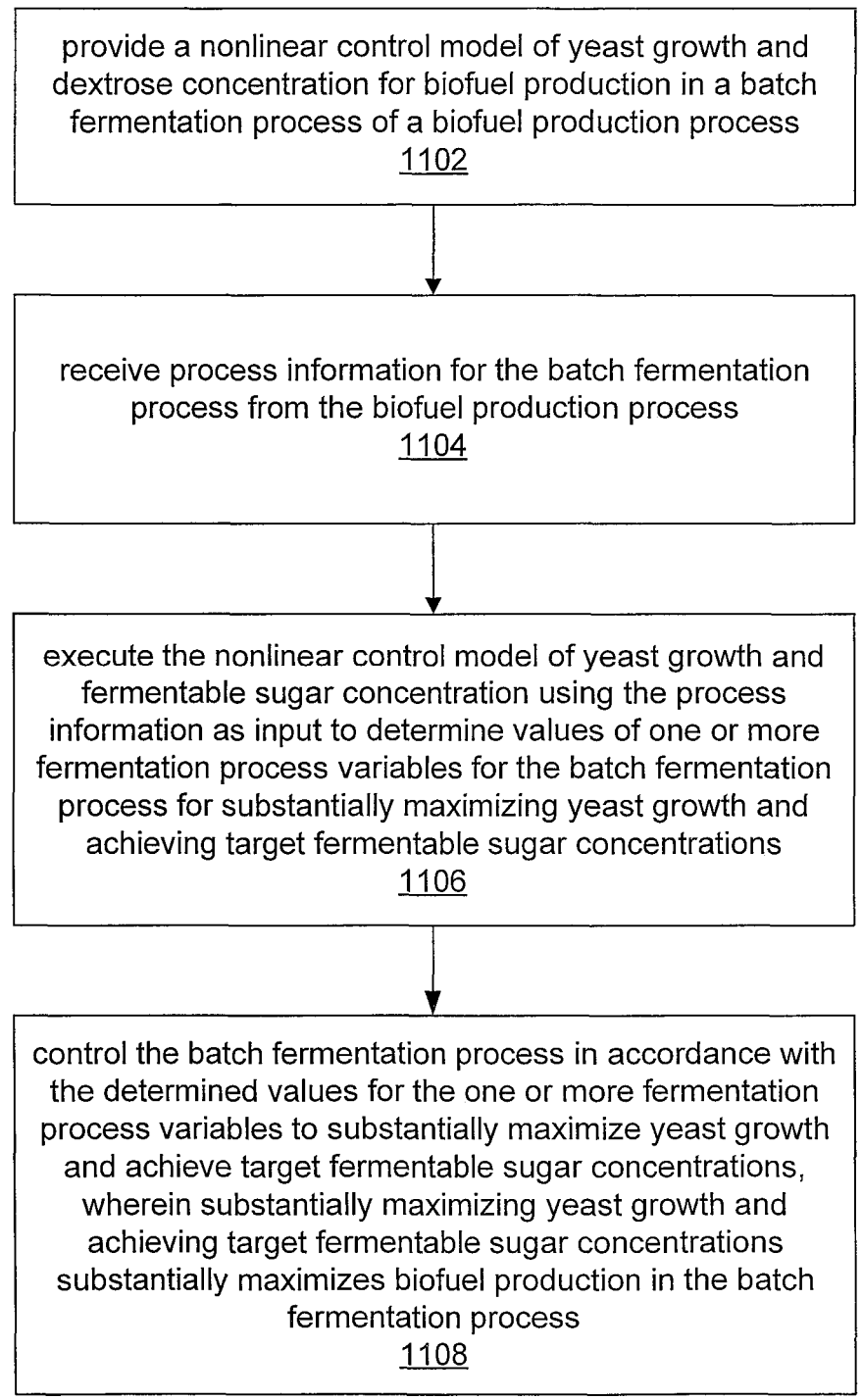
FIG. 11 is a high-level flowchart of a method for maximizing biofuel production via control of yeast growth in a batch fermentation process in a biofuel production process, according to one embodiment.

FIG. 11—Method for Managing a Batch Fermentation Process in a Biofuel Production Process FIG. 11 is a high-level flowchart of a computer-implemented method for managing a fermentation process of a biofuel production process utilizing model predictive control (MPC), according to one embodiment. As will be described below in detail, the method may include receiving process information for the batch fermentation process, and using nonlinear model predictive control with the received process information as input to substantially maximize yeast growth in the batch fermentation process, where substantially maximizing yeast growth substantially maximizes biofuel production in the batch fermentation process. In various embodiments, some of the method elements shown may be performed concurrently, in a different order than shown, or may be omitted. Additional method elements may also be performed as desired. As shown, this method may operate as follows.

In 1102, a nonlinear control model of yeast growth and fermentable sugar concentration for biofuel production in a batch fermentation process of a biofuel production process may be provided. For example, the nonlinear control model of yeast growth and fermentable sugar concentration may be based on, or derived from, the fundamental model described above, or a variant thereof. As noted above in the definition of terms, a control model is an input/output representation of a system or process that determines how much an output changes when an input is changed, and may include instantaneous (steady-state) models as well as dynamic models, as defined above. Control models may be univariate (single input effect a single output) or multivariate (multiple inputs affecting multiple outputs).

In 1104, process information for the batch fermentation process may be received, e.g., from the biofuel production process. In various embodiments, this process information may originate from various different sources. For example, the process information may include one or more of: measured properties of the batch fermentation process (e.g., temperature, pressure, water temperature, etc.); property values determined by a laboratory, referred to a laboratory data, (e.g., temperature, pH, sugar concentrations (e.g., DP4, DP3, maltose, glucose, fructose, galactose, lactose, and/or sucrose), byproducts (e.g. lactic acid, acetic acid, and glycerol) and ethanol), which may result from testing various parameters at various times throughout the batch; and/or inferred or computed values, e.g., provided by virtual online analyzers, described in more detail below.

In 1106, the nonlinear control model of yeast growth and fermentable sugar concentration may be executed using the process information as input to determine values of one or more fermentation process variables for the batch fermentation process for substantially maximizing yeast growth and achieving target fermentable sugar concentrations. The one or more fermentation process variables preferably include fermentation temperature (i.e., fermenter temperature) and/or enzyme flow, i.e., a rate of enzyme flow to the fermentation process, where, as noted above, the enzyme operates to convert starches to fermentable sugars, e.g., dextrose, maltose, fructose, galactose, lactose, and/or sucrose. Other fermentation process variables may also be included as desired, e.g., mash feed to fermenters, pH, or any other fermentation process variable.

Finally, in 1108, the batch fermentation process may be controlled in accordance with the determined values for the one or more fermentation process variables to substantially maximize yeast growth and achieve target fermentable sugar concentrations, where substantially maximizing yeast growth and achieving target fermentable sugar concentrations substantially maximizes biofuel production in the batch fermentation process.

There are a number of ways the control model may be used to determine these values. For example, in one embodiment, an objective may be specified, e.g., an objective function that specifies substantially maximizing yeast growth, and the target fermentable sugar concentrations (and possibly other objectives). The objective function may thus specify desired values or behavior of one or more controlled variables for the batch fermentation process. Executing the nonlinear control model of yeast growth and fermentable sugar concentration may include an optimizer (e.g., included in a model predictive controller) executing the nonlinear control model of yeast growth and fermentable sugar concentration in an iterative manner to solve the object function, thereby determining the values for the one or more fermentation process variables, also referred to as manipulated variables. In other words, a model predictive controller may execute the model (via an optimizer or analogous component) in an iterative manner, varying the values of manipulated variables until the objective function is solved, possibly subject to one or more constraints.

In some embodiments, a system implementing the control techniques disclosed herein may include a computer system with one or more processors, and may include or be coupled to at least one memory medium (which may include a plurality of memory media), where the memory medium stores program instructions according to embodiments of the present invention. In various embodiments, the controller(s) discussed herein may be implemented on a single computer system communicatively coupled to the biofuel plant, or may be distributed across two or more computer systems, e.g., that may be situated at more than one location. In this embodiment, the multiple computer systems comprising the controller(s) may be connected via a bus or communication network.

Figure 12:
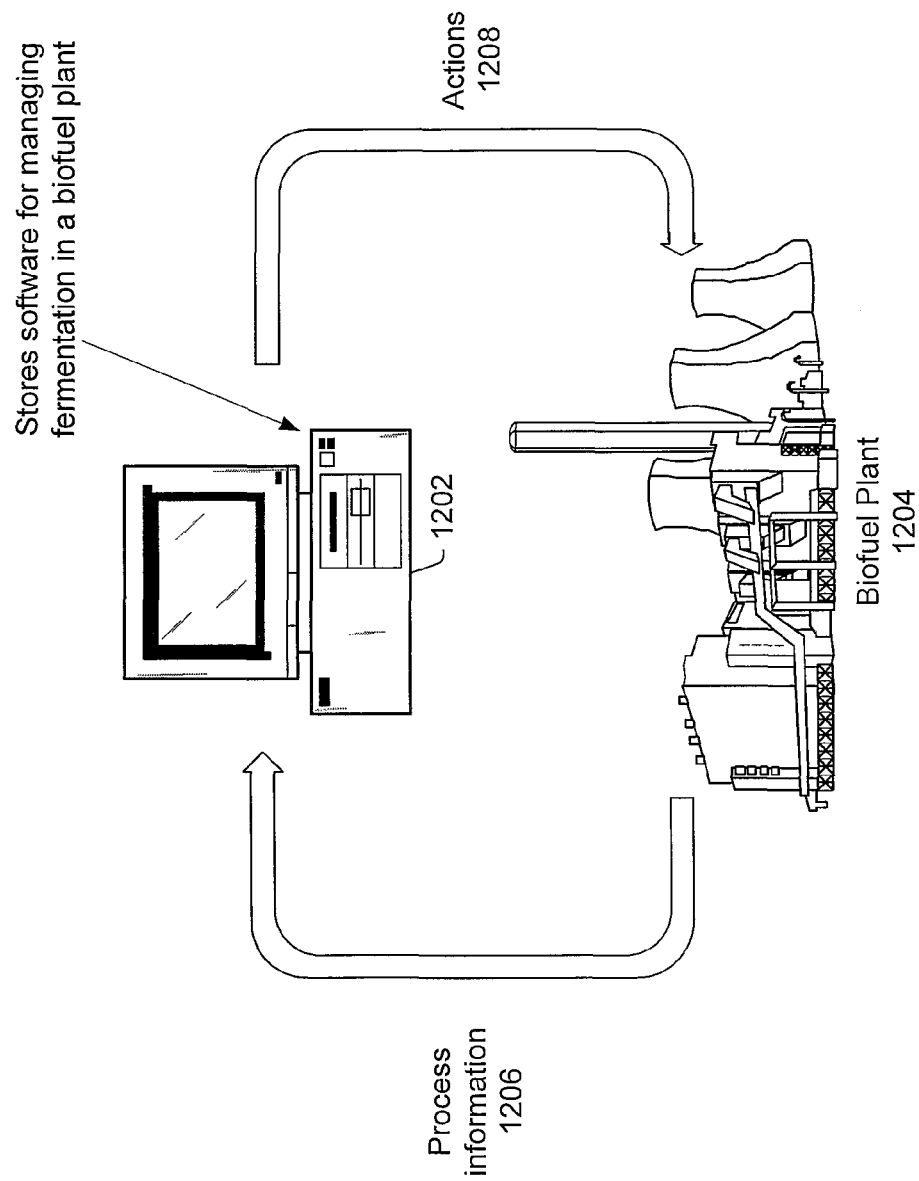
FIG. 12 is a simplified view a system for performing model predictive control of a biofuel production process, according to one embodiment.

FIG. 12 illustrates a simplified view of an automated control system for a biofuel production plant 1204. As shown, the system may include one or more computer systems 1202 which interact with the biofuel plant 1204 being controlled. The computer system 1202 may represent any of various types of computer systems or networks of computer systems which execute software program(s) according to various embodiments of the invention. As indicated, the computer system stores (and executes) software for managing fermentation in the biofuel plant 1204. The software program(s) may perform various aspects of modeling, prediction, optimization and/or control of the fermentation process. Thus, the automated control system may implement predictive model control of fermentation in the biofuel plant or process. The system may further provide an environment for making optimal decisions using an optimization solver, i.e., an optimizer, and carrying out those decisions, e.g., to control the plant.

One or more software programs that perform modeling, prediction, optimization and/or control of the plant 1204 (particularly, the fermentation process) may be included in the computer system 1202. Thus, the system may provide an environment for a scheduling process of programmatically retrieving process information 1206 relevant to the fermentation process of the plant, and generating actions 1208, e.g., control actions, to control the fermentation process, and possibly other processes and aspects of the biofuel plant or process.

The one or more computer systems 1202 preferably include a memory medium on which computer programs according to the present invention are stored. The term "memory medium" is intended to include various types of memory or storage, including an installation medium, e.g., a CD-ROM, or floppy disks, a computer system memory or random access memory such as DRAM, SRAM, EDO RAM, Rambus RAM, etc., or a non-volatile memory such as a magnetic medium, e.g., a hard drive, or optical storage. The memory medium may comprise other types of memory as well, or combinations thereof. In addition, the memory medium may be located in a first computer in which the programs are executed, or may be located in a second different computer which connects to the first computer over a network. In the latter instance, the second computer provides the program instructions to the first computer for execution.

Also, the computer system(s) 1202 may take various forms, including a personal computer system, mainframe computer system, workstation, network appliance, Internet appliance or other device. In general, the term "computer system" can be broadly defined to encompass any device (or collection of devices) having a processor (or processors) which executes instructions from a memory medium.

The memory medium (which may include a plurality of memory media) preferably stores one or more software programs for performing various aspects of model predictive control and optimization. The software program(s) are preferably implemented using component-based techniques and/or object-oriented techniques. For example, the software program may be implemented using ActiveX controls, C++ objects, Java objects, Microsoft Foundation Classes (MFC), or other technologies or methodologies, as desired. A CPU, such as the host CPU, executing code and data from the memory medium comprises a means for creating and executing the software program according to the methods or flowcharts described below. In some embodiments, the one or more computer systems may implement one or more controllers, as noted above.

Figure 13A:
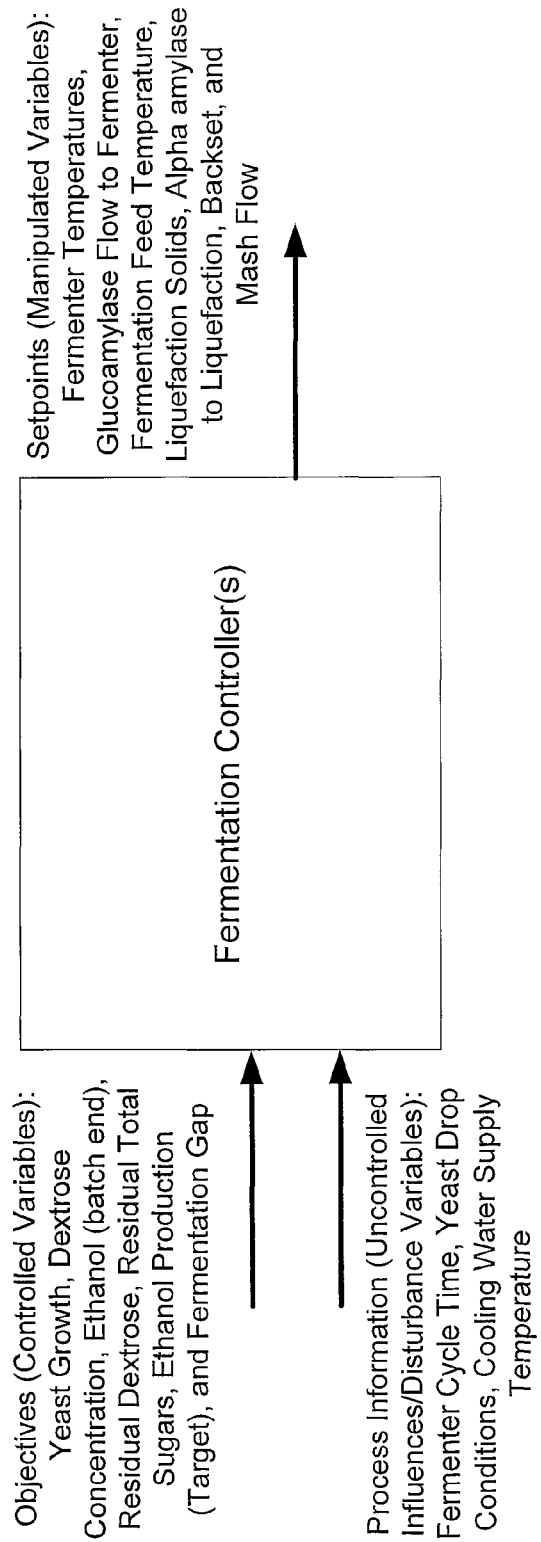
FIG. 13A illustrates model predictive control of fermentation in a biofuel production process, according to one embodiment.

FIG. 13A is a high-level illustration of a fermentation controller, according to one embodiment of the present invention. As FIG. 13A shows, the fermentation controller may receive various objectives, e.g., specified in an objective function, including, for example, one or more of: yeast growth, fermentable sugar (e.g., dextrose) concentrations, end of batch ethanol, residual dextrose, residual total sugars, ethanol production (target), and fermentation gap, among others. As FIG. 13A also shows, process information provided to the controller as input may include any of such uncontrolled influences or disturbance variables as: fermenter cycle time, yeast drop conditions, and cooling water supply temperature, among others. The fermenter controller may execute the control model (iteratively) to determine setpoints (possibly including target trajectories) for manipulated variables whereby the fermentation batch process may be controlled. For example, as FIG. 13A indicates, examples of manipulated variables include: fermenter temperatures, enzyme (glucoamylase) flow to fermenter, fermentation feed temperature, liquefaction solids, enzyme (alpha amylase) flow to liquefaction, backset, and mash flow, among others.

In some embodiments, the control model of yeast growth and fermentable sugar concentration may include a plurality of models, and/or the model predictive controller may include multiple controllers. For example, in one embodiment of the model predictive control approach described herein, the control structure (the fermentation controller of FIG. 13A) may include a main control structure or controller, operable to provide control of key objective variables, and a sub-control structure, operable to provide process variable control. It should be noted however, that in other embodiments, any numbers of models and/or controllers may be used as desired, the dual controller/model version described herein being but an exemplary embodiment.

Figure 13B:
FIG. 13B illustrates model predictive control of yeast growth and fermentable sugar (e.g., dextrose) concentrations to maximize biofuel production, including determination of desired temperature and enzyme concentration trajectories, according to one embodiment.

FIG. 13B is a high-level block diagram illustrating such a main controller, according to one embodiment. As FIG. 13B shows, in this embodiment, the main controller receives objectives, e.g., in the form of an objective function, specifying values or behaviors of controlled variables, such as, for example, substantially maximum yeast growth and optimum fermentable sugar levels, among others, as well as process information, described above. The controller may include and/or use a control model that expresses relationships between yeast growth/fermentable sugar concentrations, and temperature/enzyme concentration for the fermentation process, and may execute this model in an iterative manner (e.g., via an optimizer) to determine values of the manipulated variables that result in the specified objectives (or come as close as possible to meeting these objectives). Note that this control is accomplished via a nonlinear model predictive control algorithm.

The following summarizes the functionality of the main controller, according to one embodiment:

Main Controller:
    Controlled Variables:
        Yeast Growth [maximize], and
        Fermentable Sugar (dextrose) concentration [desired value].
    Manipulated Variables:
        Fermenter Temperature, and
        Concentration of Enzyme (e.g., GlucoAmylase) in fermenter.
    Disturbance Variables:
        Feed Mash Solids,
        Volume of Mash in fermenter, and
        Ethanol concentration in fermenter.

The nonlinear model predictive control algorithm uses the control model to move the manipulated variables to meet control objectives, which are (as noted above): substantially maximize yeast growth, and control fermentable sugar (e.g., dextrose) concentration to a desirable level. Note that the desired trajectories (of the manipulated variables, e.g., temperature and enzyme concentration) are calculated in the main control algorithm.

Figure 14:
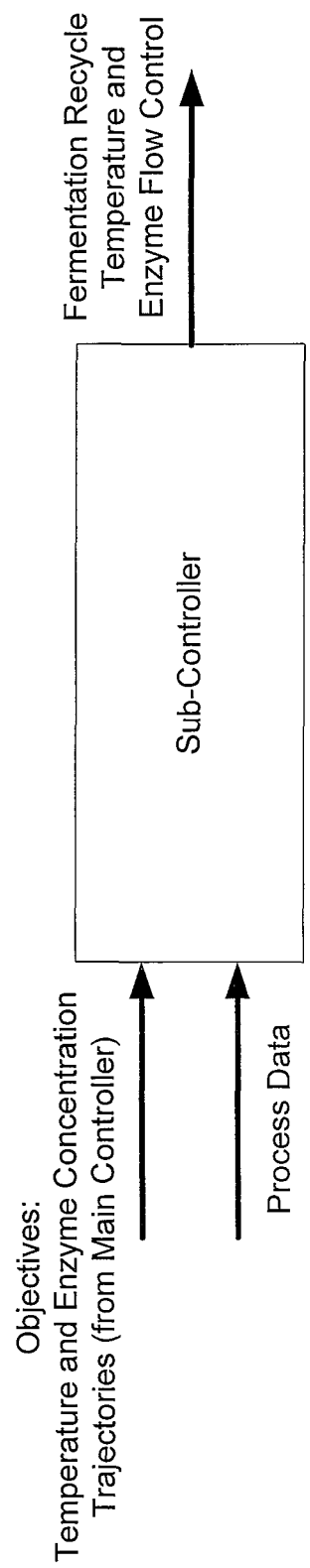
FIG. 14 illustrates model predictive control of fermentation tank temperature and enzyme concentration trajectories to maximize yeast growth and optimize fermentable sugar (e.g., dextrose) concentrations to maximize biofuel production, including determining fermentation recycle or fermenter cooler return temperature, and enzyme flow control, according to one embodiment.

As mentioned above, in some embodiments, the fermentation controller may also include a sub-controller, that may be operable to receive the determined values of the manipulated variables from the main controller, e.g., as objectives, and determine control moves to achieve these objectives. FIG. 14 is a high-level block diagram illustrating such a sub-controller, according to one embodiment. As FIG. 14 shows, in this embodiment, the sub-controller receives objectives, e.g., in the form of an objective function, specifying values or behaviors of controlled variables, such as, for example, the target temperature and enzyme concentration values (or trajectories) determined by the main controller, among others, as well as process information, described above. The sub-controller may include and/or use a control model that expresses process relationships between temperature/enzyme concentration for the fermentation process, and means, e.g., control flows, used to achieve these targets, e.g., fermenter cooler return temperature (e.g., fermentation recycle temperature), slurry mash temperature, and enzyme flow, and, similar to the main controller, may execute this model in an iterative manner (e.g., via an optimizer) to determine values of the manipulated variables that result in the specified objectives (or come as close as possible to meeting these objectives).

Thus, while the main controller calculates the fermenter temperature and enzyme concentration at any given time to meet high-level control objectives (i.e., desired temperature and enzyme trajectories), the control of these two process variables is accomplished via a lower level sub-controller. Note that this control is also accomplished via a nonlinear model predictive control algorithm, where the model predictive control algorithm uses the manipulated variables, e.g., fermenter cooler return temperature and enzyme flow, to meet the control objectives.

The following summarizes the functionality of the sub-controller, according to one embodiment:

Sub-Controller:
Controlled Variables:
Fermenter Temperature [desired trajectory], and
Concentration of Enzyme in fermenter [desired trajectory].
Manipulated Variables:
Fermenter Cooler return temperature,
Slurry Mash Feed Temperature, and
Flow of Enzyme (glucoamylase) to fermenter.
Disturbance Variables:
Mash Flow to fermenters, and
Heat of ethanol conversion reaction.

The nonlinear model predictive control algorithm uses the control model to move the manipulated variables to meet control objectives, which are (as noted above): follow a desired trajectory for fermenter temperature, and follow a desired trajectory for concentration of enzyme in fermenter.

It should be noted that the above approach can be applied to biofuel production facilities with any number of fermentation units. For example, FIGS. 15 and 16 illustrate exemplary control matrices with respect to a three fermenter process.

FIG. 15 illustrates one embodiment of a control matrix for the main controller of FIG. 13B. As FIG. 15 shows, this control matrix displays controlled variables (CVs), including yeast growth (Yeast_n, where n=1, 2, 3) and dextrose concentrations (C_Dextrose_n) for each of three fermenters, as well as manipulated variables (MVs), including temperature (T_n), enzyme concentration (specifically glucoamylase (GA))(V_GA_n), ethanol concentration (C_Ethanol_n), and solids concentration (C_Solids_n), for each of the three fermenters, among others. Other inputs acting as either MVs or DVs are also contemplated, such as nitrogen or ammonia addition, yeast addition (flow) or other controllers per other various specific biofuel process configurations.

FIG. 16 illustrates a control matrix for the sub-controller of FIG. 14. As FIG. 14 shows, this control matrix displays CVs, including fermenter temperature (T_n), and enzyme concentration (V_GA_n) for each of the three fermenters, as well as MVs, including cooler return temperature (T_n_Cooler), and reaction rate (H_n_Rx) for each of the three fermenters, and slurry temperature (T_Slurry), flow rate of enzyme (F_GA), and flow rate of slurry mash (F_Slurry).

Such matrices are well-known in the art of model predictive control, and so further discussion is not needed.

Figure 17:
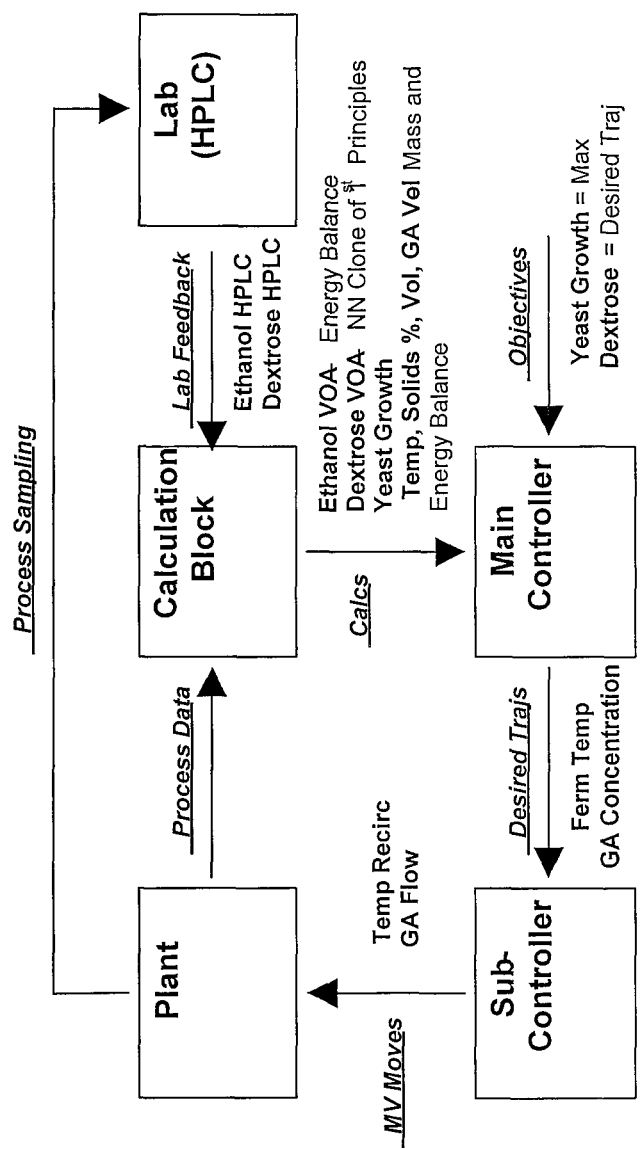
FIG. 17 illustrates high-level operation of a model predictive control system, according to one embodiment of the present invention.

One embodiment of the overall control structure is illustrated in FIG. 17. It should be noted that the particular architecture or functional partitions shown in FIG. 17 is meant to be exemplary only, and that other architectures or functional partitions may be used as desired. As FIG. 17 shows, in this embodiment, a calculation block may be provided process data from the plant or process, as well as laboratory data from a laboratory (e.g., generated by HPLC (High Purity Liquid Chromatography)), where the process data and laboratory data are referred to collectively as process information. As noted above, in some embodiments, data may also be provided from inferred property models, also referred to as virtual online analyzers, discussed below. The calculation block may calculate various attributes and send these calculations to the main controller. More specifically, in some embodiments, the calculation block may receive the process data and lab data as input, and execute VOAs to produce VOA values (inferred property values), perform general data conditioning, calculate gains for the controller and perform all the logic necessary to control multiple fermenters. As shown, examples of these calculations may include various computations, such as: ethanol VOA values (computed from energy balance), dextrose VOA values (where the dextrose VOA may be a neural network clone of the fundamental model (also referred to as a first principles model)), yeast growth, temperature, solids %, volume, and enzyme volume, among others. As also shown, objectives may also be provided to the main controller, e.g., yeast growth=maximum, and dextrose=desired trajectory. The main controller may determine desired trajectories for fermentation temperature and enzyme concentration, as described above in detail, and provide these values to the sub-controller, which may determine MV moves, e.g., regarding fermenter cooler return temperature, and enzyme flow, and implement the moves to control the process accordingly.

Examples of process data provided to the calculation block may include any of various attributes of the fermentation process, such as, for example, fermenter temperature, slurry mash feed temperature, slurry mash feed rate, enzyme flow rate, fermenter level, fermenter cooler return temperature, fermenter batch time, and valve positions, among others.

Note that in some embodiments, a principal factor in the calculation of yeast growth is fermenter heat balance. In other words, embodiments of the present invention utilize a key correlation between fermenter heat balance (metabolic heat generated), yeast activity, and biofuel production in a batch fermenter. This relationship was principally identified between the fundamental fermentation models, yeast growth and the fermenter heat balance, where it was found that inferred quality of yeast growth matches the developed batch fermentation models on yeast activity and biological fermenter sampling, and is strongly correlated to fermenter heat balance.

It should noted that the particular terminology used herein regarding this relationship, i.e., yeast activity/productivity correlated to fermenter heat balance, is not intended to limit the scope of the invention to any specific nomenclature, but rather, embodiments of the present invention are contemplated to cover the principal concept of correlating biological metabolic activity with fermenter heat balance, and the corresponding use of this correlation to control fermentation. Said another way, this correlation and its use are independent of the vocabulary used with respect to the intermediate function described herein as yeast growth.

Control Models

As indicated above, control models are needed for the predictive function of the main control algorithm. These models are nonlinear by nature and may be determined using the fundamental kinetic model. More specifically, in one embodiment, the nonlinear control models may be obtained by "cloning" the kinetic model, which has been parameterized using process data. This procedure may include solving the kinetic model over a wide range of operating parameters. The solution values may then be used to create nonlinear control models. These models can be, but are not limited to, neural network models. For example, support vector machines, or other nonlinear model technologies, or combinations of model types, may be used as desired.

Thus, nonlinear control models may be obtained by exercising the fundamental kinetic model over a wide operating range, where the kinetic model is parameterized using plant data. In some embodiments, these models may be built using the following relationships:

Yeast Growth Function←Concentration of Ethanol,
  Fermenter Temperature,
  Mash Slurry Solids,
  Concentration of enzyme (glucoamylase)
    in fermenter, and
  Volume of mash in fermenter.
Dextrose in Fermenter←Concentration of Ethanol,
  Fermenter Temperature,
  Mash Slurry Solids,
  Concentration of enzyme (glucoamylase)
    in fermenter, and
  Volume of mash in fermenter.

Figure 18:
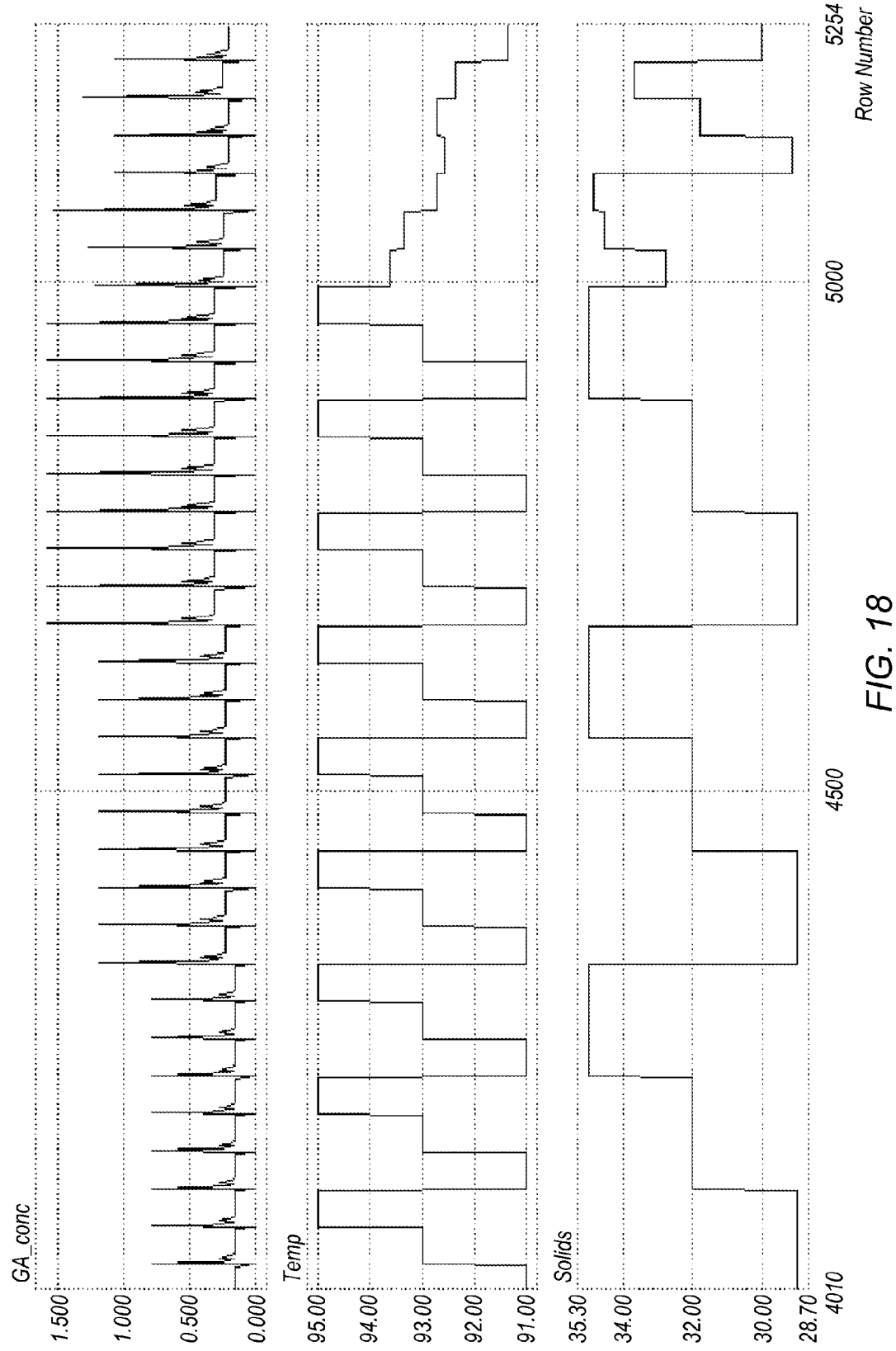
FIG. 18 illustrates an exemplary testing procedure for identifying nonlinear models (e.g., cloning) from a fundamental kinetic model, according to one embodiment.

In other words, the various parameters on the right may be used to determine the yeast growth function and the dextrose concentration in the fermenter. An example of the testing procedure for identifying nonlinear models from a fundamental (kinetic) model is shown in FIG. 18, where, as may be seen, the designed behavior of various parameters is displayed, including enzyme concentration (GA-conc), temperature (Temp), and solids (Solids).

Virtual Analyzers for the Fermentation Process

As indicated above, in some cases, there may be some fermentation attributes or variables that are not readily measurable. For example, to date, there are no reliable methods for online analysis of key fermentation variables, particularly ethanol concentration and fermentable sugar (e.g., dextrose) concentration. In order to overcome this limitation, virtual analyzers (VOAs) have been developed to predict control variables needed by the above-described control strategy. More specifically, VOAs have been developed from process data and fundamental process knowledge to accurately predict key fermentation variables: ethanol concentration, fermentable sugar (e.g., dextrose) concentration and yeast growth, although other VOAs may certainly be used as desired. Thus, in some embodiments, predicted values for unmeasured attributes of the batch fermentation process may be computed by one or more predictive models (e.g., VOAs). In some embodiments, these predictive models may be dynamic predictive models, e.g., where the models are dynamically updated, e.g., based on current process conditions.

Figure 19:
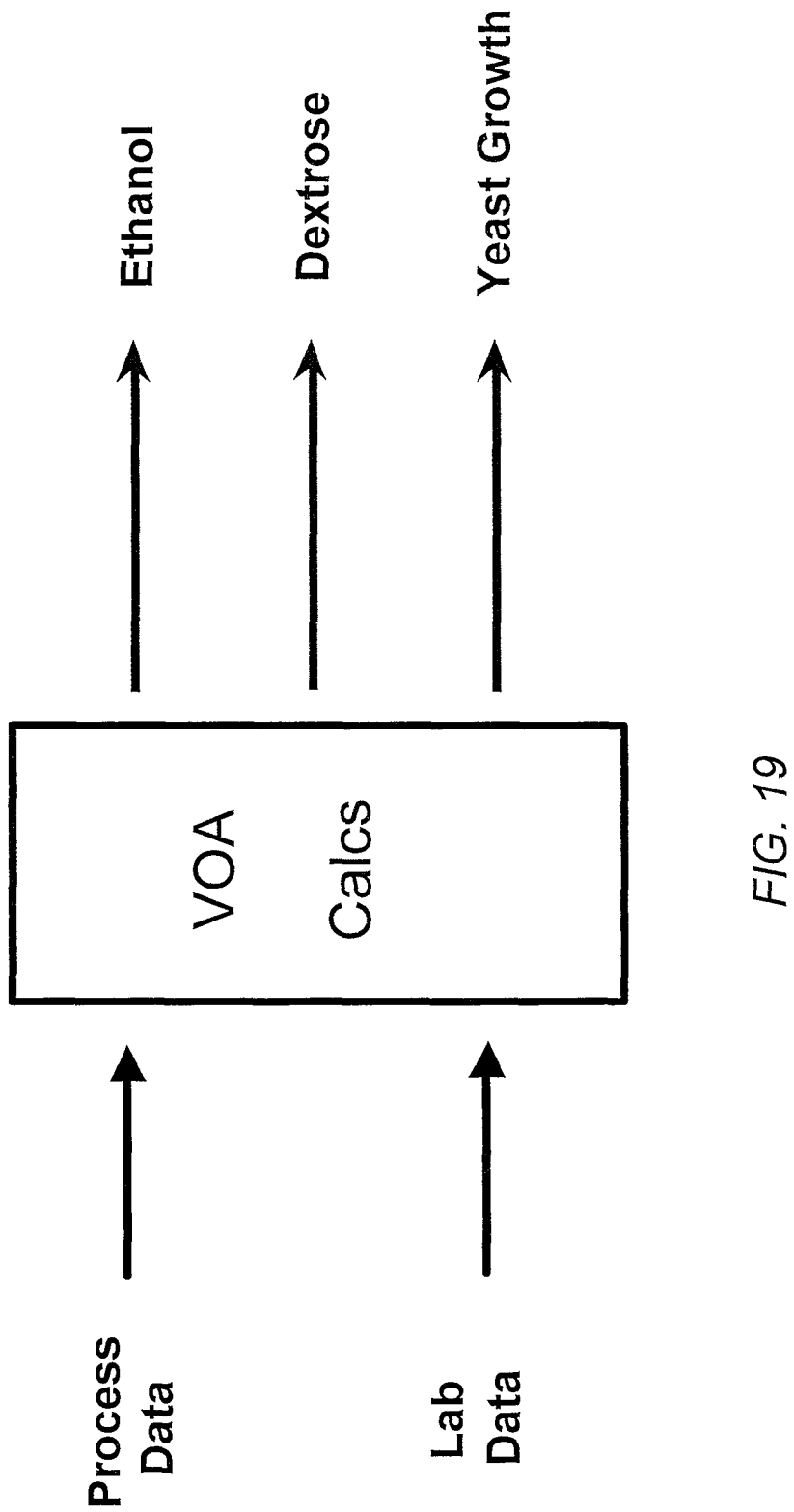
FIG. 19 illustrates a virtual online analyzer (VOA) for estimating ethanol concentration, dextrose concentration, and yeast growth in the batch fermentation process, according to one embodiment.

FIG. 19 illustrates the use of VOAs to compute these variables, where, as may be seen, process data and laboratory data are provided as input to the VOAs, which then compute values for ethanol, dextrose, and yeast growth. In some embodiments, a respective VOA may be used to compute values for each of these three process variables.

In one embodiment, the ethanol concentration VOA for each fermenter may be calculated from the energy balance. The ethanol production at any time may be inferred from the energy balance. The total ethanol in the fermenter is then an integration of this value through time. The VOA may be updated using plant HPLC laboratory results entered in by the operator (or received programmatically). Biasing calculations may be used for each fermenter so that the ethanol VOA remains consistent with the laboratory results. The following illustrates the use of various measured quantities to compute ethanol concentration, according to one embodiment. It should be noted that in some embodiments, all these quantities relate to energy balance.

Ethanol Concentration VOA Values←Mash Feed Temperature,
  Mash Feed Flow,
  Fermenter Cooler return temperature,
  Fermenter Recycle Flow,
  Temperature of mash in fermenter, and
  Volume of mash in fermenter.

Figure 20:
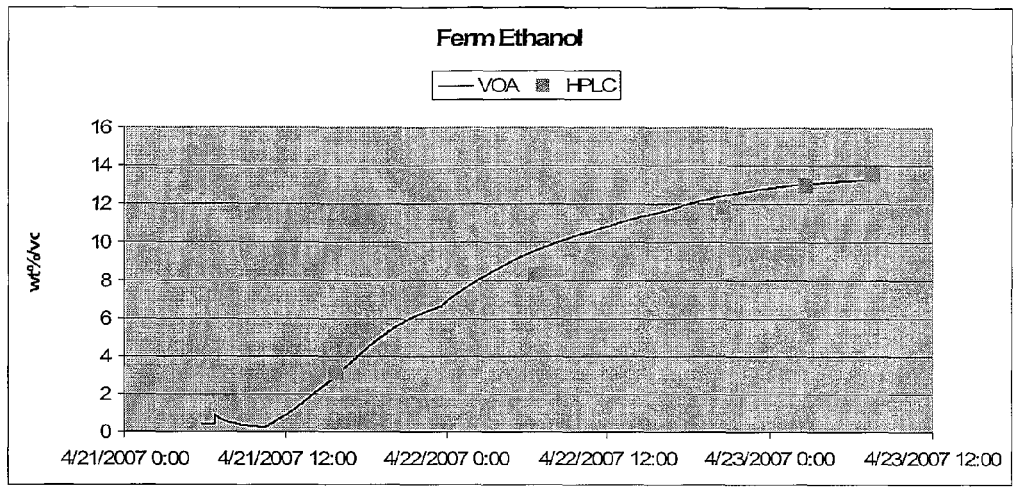
FIGS. 20 and 21 compare VOA estimations of ethanol and dextrose concentration with laboratory measurements, according to one embodiment.

FIG. 20 illustrates VOA computations for ethanol concentrations compared to laboratory results (HPLC). As may be seen, the VOA values closely track the laboratory results.

In some embodiments, the dextrose VOA maybe a neural network cloned from the fundamental (kinetic) model described above, where "cloning" refers to the technique described above in identifying or determining the process control models. Laboratory biasing may also come from plant HPLC laboratory results entered in by the operator (or received programmatically).

The following illustrates the use of various measured quantities to compute dextrose (or any other fermentable sugar) concentration, according to one embodiment. It should be noted that in some embodiments, all these quantities relate to inputs to the kinetic model.

Dextrose Concentration VOA Values←Concentration of Ethanol,
  Fermenter Temperature,
  Mash Slurry Solids,
  Concentration of enzyme
    (glucoamylase), and
  Batch Time.

Figure 21:
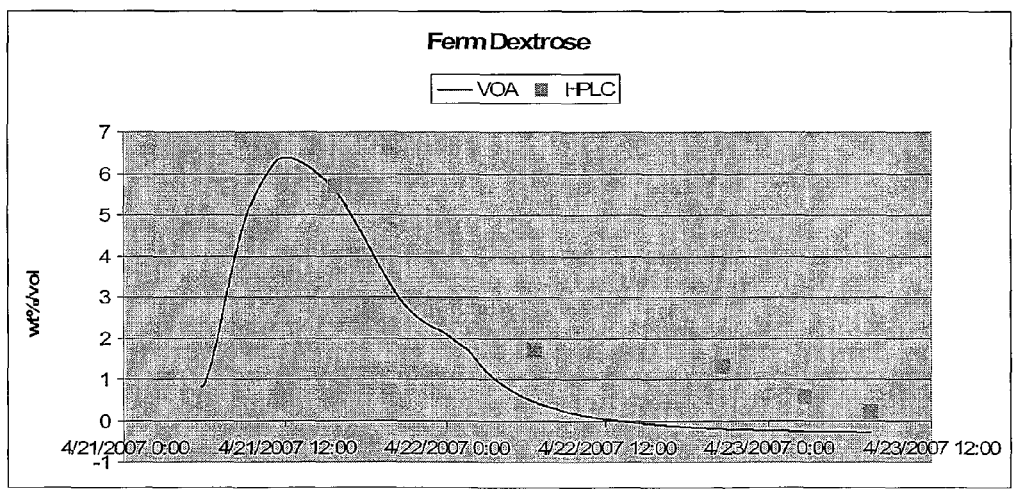

FIG. 21 illustrates VOA computations for dextrose concentrations compared to laboratory results (HPLC). As with the ethanol VOA, the VOA values closely track the laboratory results, particularly in the region of substantially maximum production.

The yeast growth function, as discussed above, is the rate of growth minus the rate of death of yeast in the fermenter. In some embodiments, the yeast growth VOA may be a clone of the yeast growth calculated by the fundamental model with a neural network, e.g., using the technique described above with respect to determining or identifying the process control models. The following illustrates the use of various measured quantities to compute yeast growth, according to one embodiment. It should be noted that in some embodiments, all these quantities relate to inputs to the kinetic model.

Yeast Growth Function VOA Values←Concentration of Ethanol,
  Fermenter Temperature,
  Mash Slurry Solids, and
  Concentration of enzyme
    (glucoamylase).

It should be noted that whereas the descriptions herein often refer to dextrose concentrations, dextrose is but one of numerous fermentable sugars that may be involved in biofuel production, and that the references to dextrose are intended to be exemplary. In other words, the techniques disclosed herein are also intended to be applicable to any other fermentable sugars involved in biofuel production, as well.

Extension of Control Algorithm

In some embodiments, temperature manipulation of biofuel fermentation units may be accomplished using cooling water through a heat exchanger. In some cases, additional cooling capacity is available by use of an external chilled water unit. Incorporation of the chilled water is a natural extension of the control strategy disclosed herein, and is contemplated as falling within the scope of the present invention.

Additional Controlled Variables

In some embodiments, the overall fermentation control strategy may include the control of several process inputs outside of the main fermentation control algorithm, such as, for example, the liquefaction enzyme addition (e.g., alpha amylase) and the backset flow to the fermenters. This control may include: alpha amylase, which may be ratio controlled based on overall corn (or other biomass) feed to the plant, and backset, which may be controlled to a setpoint as percent of overall water addition to corn (or other biomass)/water mixing tank, among others.

Figure 22:
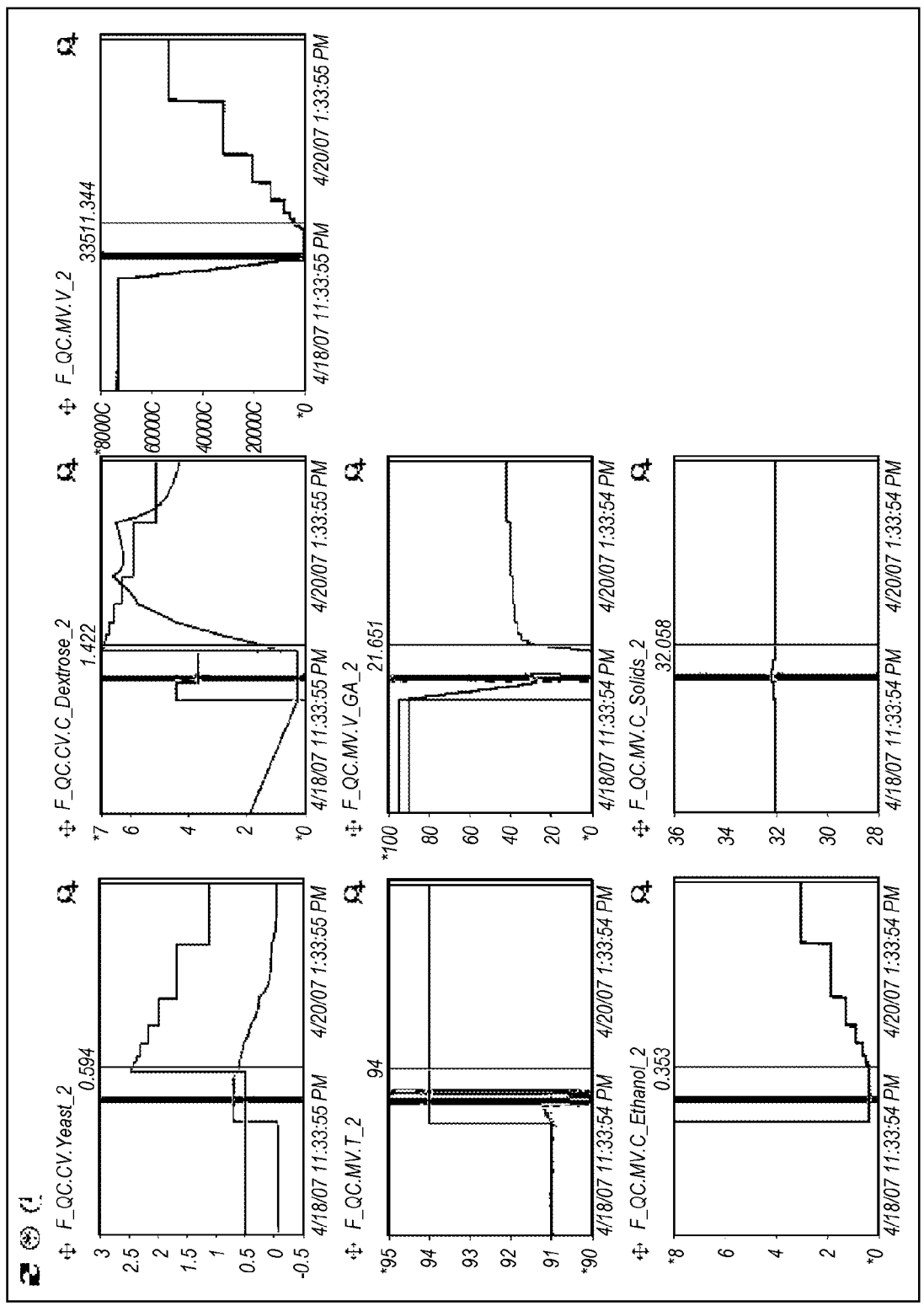
FIG. 22 is a screenshot of an exemplary graphical user interface for model predictive control of fermentation in a biofuel production process, according to one embodiment of the present invention.

FIG. 22—Graphical User Interface

In some embodiments, a graphical user interface (GUI) may be provided for creating and/or using embodiments of the present invention. FIG. 22 is a screenshot of an exemplary GUI for monitoring and/or controlling the fermentation process. As may be seen, in this embodiment, customizable views may be specified whereby an operator may monitor actual and/or derived or computed values for attributes or process variables of the fermentation process. It should be noted, however, that in other embodiments, the GUI may facilitate any other kind of monitoring or control functionality as desired.

Note that in this particular exemplary embodiment, the GUI displays plots of various parameters or variables of the fermentation process, where in each plot, data to the left of a vertical black line approximately in the middle of the plot are historical, and data to the right of the vertical black line are projected.

Figure 23:
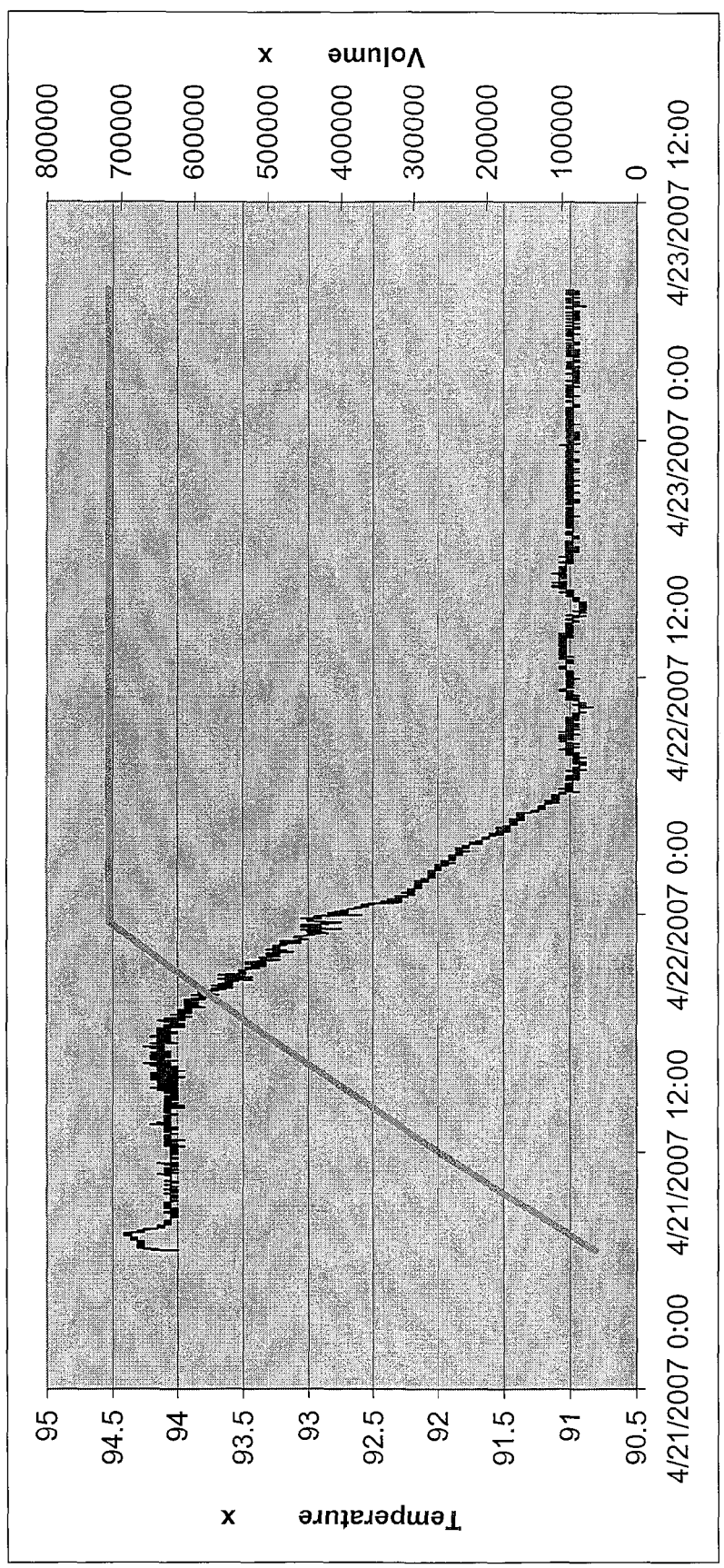
FIG. 23 illustrates an exemplary temperature profile of an industrial ethanol fermentation unit, according to one embodiment of the invention.
Figure 24:
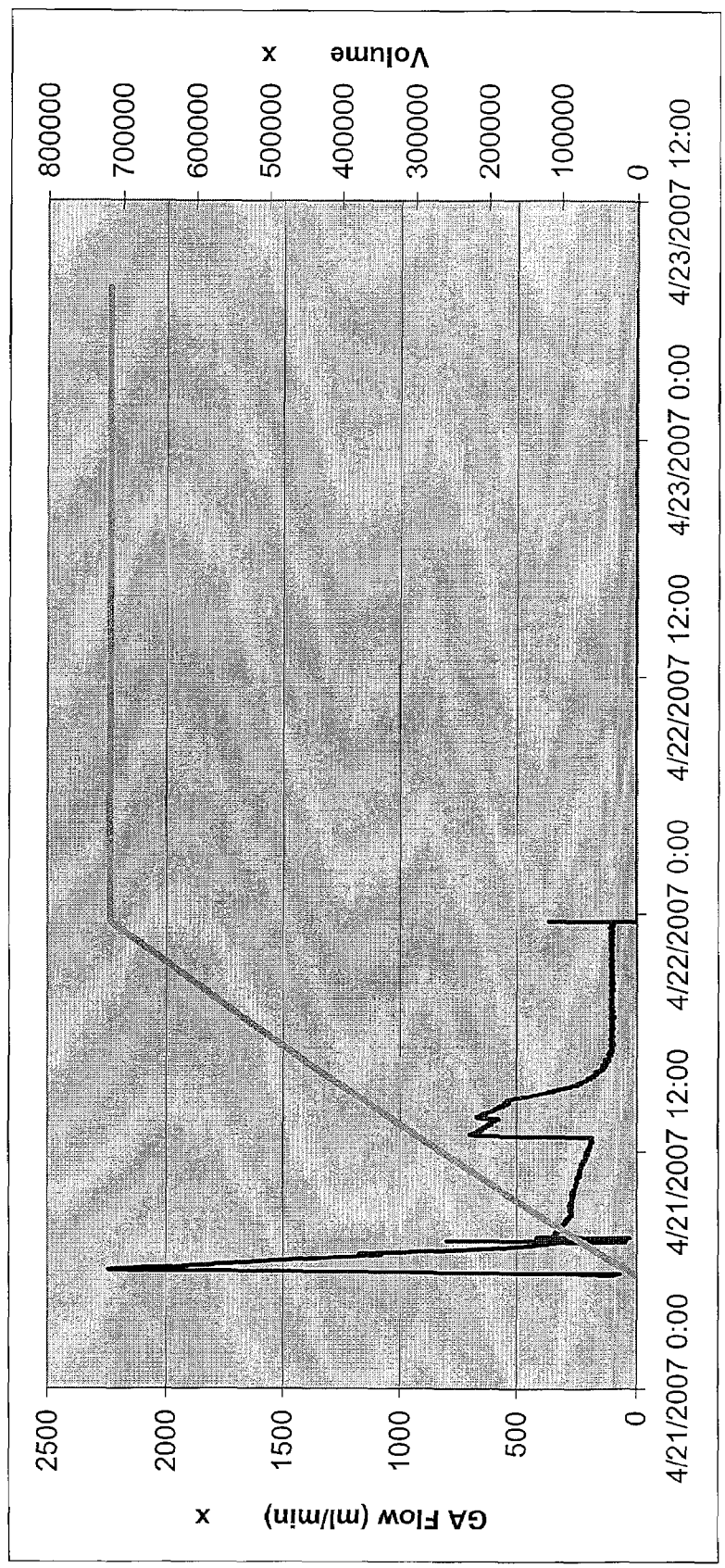
FIG. 24 illustrates a resultant enzyme flow into a fermentation tank, according to one embodiment of the invention.
Figure 25:
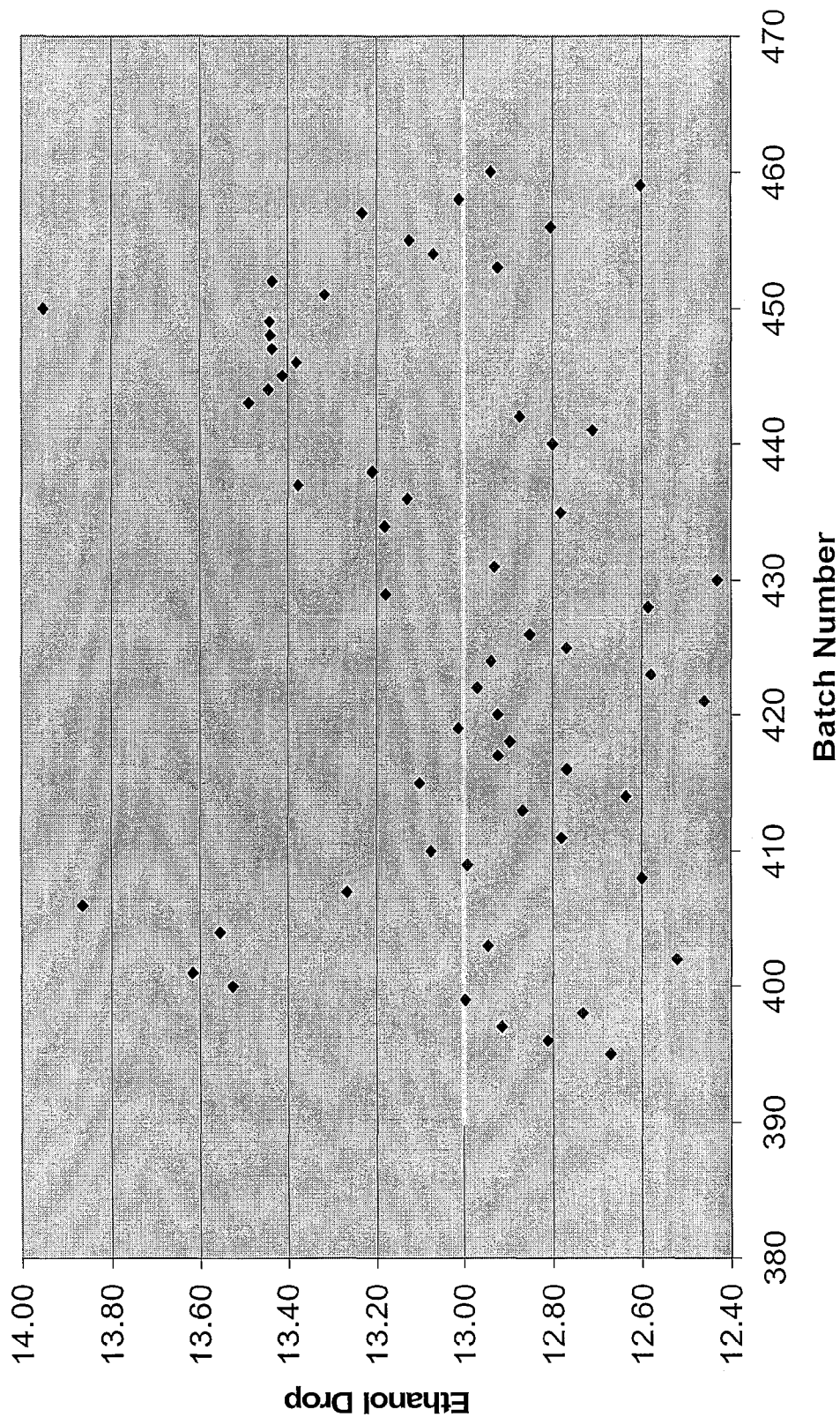
FIG. 25 illustrates the mean value and variability of ethanol after the fermentation process, without employing the advance control strategies disclosed herein.

FIGS. 23-25—Exemplary Results

FIGS. 23-25 illustrate exemplary results and benefits of the techniques disclosed herein, according to one embodiment.

FIG. 23 illustrates an exemplary temperature profile of an industrial ethanol fermentation unit under the closed-loop control methodology described herein, according to one embodiment. In this example, the temperature profile is calculated based on the maximum conditions for yeast growth. Also shown in FIG. 20 is the volume of fermentable mash in the fermentation tank over the same time period.

As may be seen, the mash volume increases steadily while the temperature is held substantially constant at ~94 degrees (F), peaking just after the temperature begins declining, and remaining steady thereafter. As FIG. 23 indicates, the temperature bottoms out at ~91 degrees. Note that once the mash volume peaks, the temperature has little or no effect (on the mash volume).

FIG. 24 illustrates a resultant enzyme (GA=glucoamylase) flow into a fermentation tank under the closed-loop control methodology described herein, according to one embodiment. Note that in typical industrial fermentation processes, the enzyme can only be added during the fill cycle.

As shown in FIG. 24, in this example case, enzyme flow increases dramatically initially, peaking at ~2250 ml/min, then rapidly decreases (with a brief burst close to the 12 hour mark) to less than 100 ml/min before ceasing at roughly the 24 hour mark. As also shown, fermentation mash volume increases steadily, then levels off at ~24 hours.

Figure 26:
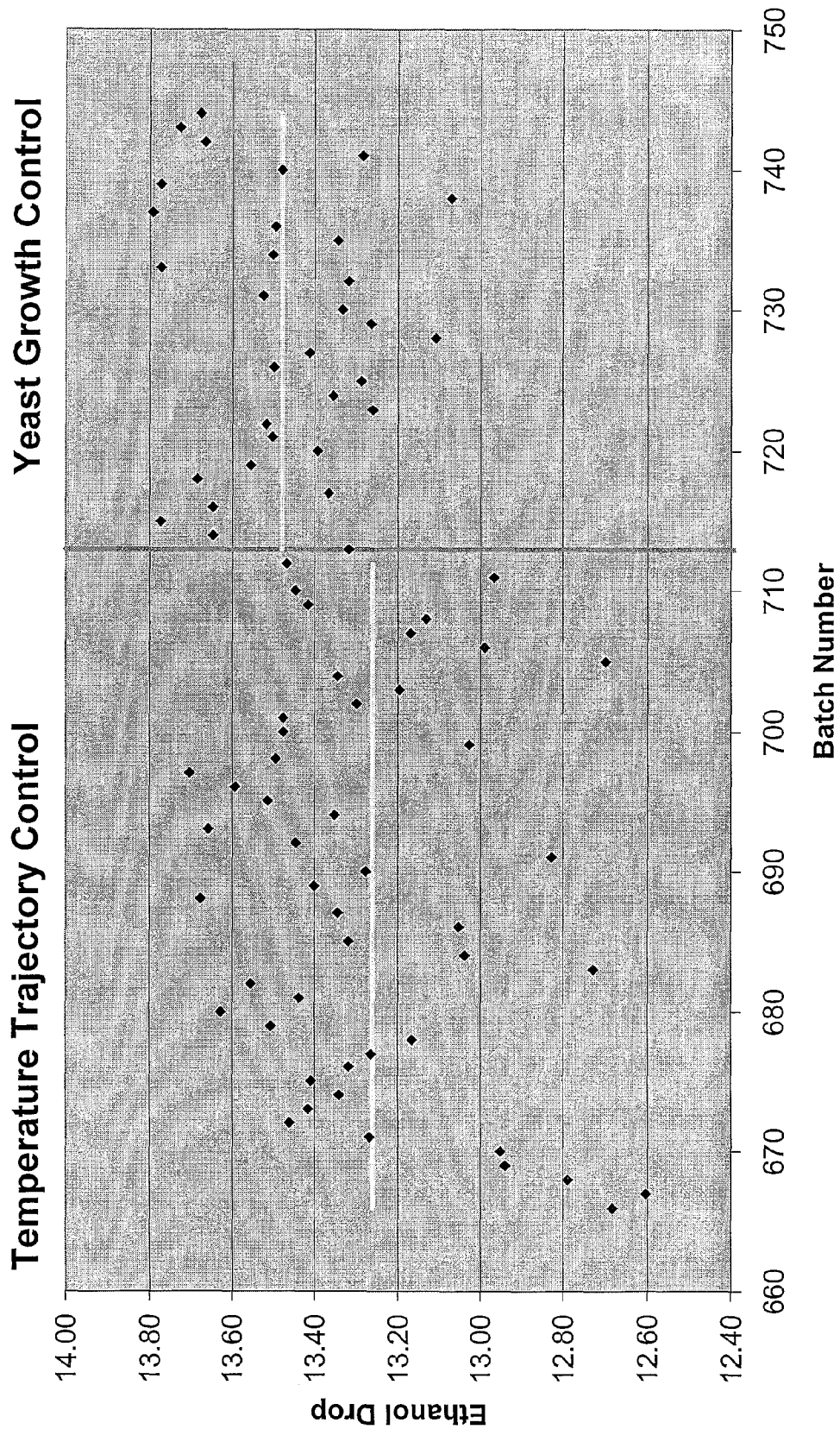
FIG. 26 illustrates a comparison of exemplary effects of the control strategy: 1) with only temperature control; and 2) with the complete control strategy as described herein, according to one embodiment.

Thus, as FIGS. 23 and 24 indicate, controlling temperature and enzyme flow rates may provide an effective means for controlling and optimizing yeast growth, reflected in mash volume, which, as explained above, controls and optimizes ethanol production. FIGS. 25 and 26 compare aspects of ethanol production without and with the control strategies described herein.

FIG. 25 illustrates the mean value and variability of ethanol after the fermentation process, without employing the advance control strategies disclosed herein. As may be seen, many batches were produced, with a wide variety of results. Note that the data show an average ethanol content of 13 wt %/vol with almost ½% variability.

FIG. 26 illustrates exemplary effects of the control strategy: 1) with only temperature control; and 2) with the complete control strategy as described herein, according to one embodiment. Note that using only temperature control, an increase in ethanol production of 0.26 wt %/vol resulted (as compared to production using prior art control strategies), with is a 2% increase over prior art techniques. However, as FIG. 26 indicates, taking advantage of the full fermentation control strategies disclosed herein, according to one embodiment, i.e., maximizing yeast growth by controlling temperature, sugar content, and enzyme flow rates, results in an increase of 0.48 wt %/vol, or a 3.7% increase over prior art techniques.

Note that the results also indicate that the variability decreased by 46%, and so the techniques described herein may also dramatically improve the reliability or consistency of the fermentation process. These performance improvements may thus have a very large economic impact on biofuel production, e.g., particularly with respect to current biofuel production plants.

Thus, various embodiments of the above systems and methods may be used to manage fermentation, e.g., batch fermentation in a biofuel production process, using model predictive control.

Although the system and method of the present invention has been described in connection with the preferred embodiment, it is not intended to be limited to the specific form set forth herein, but on the contrary, it is intended to cover such alternatives, modifications, and equivalents, as can be reasonably included within the spirit and scope of the invention as defined by the appended claims.

We claim:

1. A method for managing a batch fermentation process in a biofuel production process, comprising:
  providing a nonlinear control model of yeast growth and fermentable sugar concentration for biofuel production in a batch fermentation process of a biofuel production process, wherein yeast growth is a function of a cooler return temperature of a fermenter, metabolic heat generation in the fermenter, and a volumetric change in a fermentation tank;

receiving process information for the batch fermentation process, wherein the process information includes the fermenter cooler return temperature;

executing the nonlinear control model of yeast growth and fermentable sugar concentration using the process information as input, thereby determining target values of one or more fermentation process variables and an optimal batch temperature trajectory during filling of the fermentation tank that substantially maximizes yeast growth and achieves target fermentable sugar concentrations, wherein the one or more target values comprise a mash flow rate or a yeast addition rate; and controlling the mash flow rate or the yeast addition rate during filling of the fermentation tank in accordance with the determined target values for the one or more fermentation process variables and the optimal batch temperature trajectory.

2. The method of claim 1, wherein the nonlinear control model comprises a physics-based model including equations for the volumetric change in the fermentation tank, a yeast activation rate, a yeast growth rate, the yeast death rate, a fermentable sugar conversion rate, a dextrin conversion rate, a biofuel production rate, or an enzyme addition rate.

3. The method of claim 1, further comprising:
specifying an objective function, wherein the objective function specifies the target fermentable sugar concentrations;
wherein said executing the nonlinear control model of yeast growth and fermentable sugar concentration comprises:
an optimizer executing the nonlinear control model of yeast growth and fermentable sugar concentration in an iterative manner to solve the objective function, thereby determining the values for the one or more fermentation process variables.

4. The method of claim 1, wherein the process information further comprises one or more of:
measured attributes of the batch fermentation process;
laboratory data; or
predicted values for unmeasured attributes of the batch fermentation process computed by one or more predictive models.

5. The method of claim 1, wherein the nonlinear control model of yeast growth and fermentable sugar concentration comprises:
a nonlinear control model of yeast growth and fermentable sugar concentration as a function of fermentation temperature and enzyme concentration; and
a nonlinear control model of temperature and enzyme concentration as a function of fermenter cooler return temperature and enzyme flow.

6. The method of claim 5, wherein said executing the nonlinear control model of yeast growth and fermentable sugar concentration comprises:
executing the nonlinear control model of yeast growth and fermentable sugar concentration as a function of fermentation temperature and starch-converting enzyme concentration using the process information as input, thereby determining values of temperature and starch-converting enzyme concentration for the batch fermentation process that substantially maximize yeast growth and achieve the target fermentable sugar concentration; and executing the nonlinear control model of temperature and starch-converting enzyme concentration using the process information as input, thereby determining the values for the fermenter cooler return temperature and starch-converting enzyme flow that achieve the determined values of temperature and starch-converting enzyme concentration in the batch fermentation process.

7. The method of claim 1, wherein the batch fermentation process comprises a fed-batch process.

8. The method of claim 1, wherein the batch fermentation process comprises a pure batch process.

9. The method of claim 1, further comprising:
performing said receiving process information, said executing the nonlinear control model of yeast growth and fermentable sugar concentration, and said controlling the mash flow rate or the yeast addition rate in an iterative manner to produce the biofuel in a substantially optimal manner.

10. The method of claim 1, wherein the biofuel comprises ethanol, and wherein yeast growth is based on the following equation:

$$\text{yeast growth} = \left( \frac{\mu_x^{max}(T) y_{sugar}}{(k_{x1} + y_{EtOH})(k_{x2} + y_{sugar})} - r_d(t) \right)$$

where $\mu_x^{max}(T)$ is the theoretical maximum yeast growth rate as a function of temperature T, $y_{sugar}$ is the fermentable sugar concentration, $y_{EtOH}$ is an ethanol concentration, $k_{x1}$ is an ethanol saturation constant, $k_{x2}$ is the fermentable sugar saturation constant, and $r_d(T)$ is the yeast death rate as a function of temperature T.

11. A computer-accessible memory medium configured for managing a batch fermentation process in a biofuel production process, wherein the memory medium stores:
a nonlinear control model of yeast growth and fermentable sugar concentration for biofuel production in a batch fermentation process of a biofuel production process, wherein yeast growth is a function of a cooler return temperature of a fermenter, metabolic heat generation in the fermenter, and a volumetric change in a fermentation tank; and
program instructions, executable to perform:
receiving process information for the batch fermentation process, wherein the process information includes the fermenter cooler return temperature;
executing the nonlinear control model of yeast growth and fermentable sugar concentration using the process information as input, thereby determining target values of one or more fermentation process variables and an optimal batch temperature trajectory during filling of the fermentation tank that substantially maximizes yeast growth and achieves target fermentable sugar concentrations, wherein the one or more target values comprise a mash flow rate or a yeast addition rate; and
controlling the mash flow rate or the yeast addition rate during filling of the fermentation tank in accordance with the determined target values for the one or more fermentation process variables and the optimal batch temperature trajectory.

12. The memory medium of claim 11, wherein the nonlinear control model comprises a physics-based model including equations for the volumetric change in the fermentation tank, a yeast activation rate, a yeast growth rate, the yeast death rate, a fermentable sugar conversion rate, a dextrin conversion rate, a biofuel production rate, or an enzyme addition rate.

13. The memory medium of claim 11, wherein the program instructions are further executable to perform:
receiving an objective function, wherein the objective function specifies the target fermentable sugar concentrations;
wherein said executing the nonlinear control model of yeast growth and fermentable sugar concentration comprises:
an optimizer executing the nonlinear control model of yeast growth and fermentable sugar concentration in an iterative manner to solve the objective function, thereby determining the values for the one or more fermentation process variables.

14. The memory medium of claim 11, wherein the process information further comprises one or more of:
measured attributes of the batch fermentation process;
laboratory data; or
predicted values for unmeasured attributes of the batch fermentation process computed by one or more predictive models.

15. The memory medium of claim 11, wherein the nonlinear control model of yeast growth and fermentable sugar concentration comprises:
a nonlinear control model of yeast growth and fermentable sugar concentration as a function of fermentation temperature and enzyme concentration; and
a nonlinear control model of temperature and enzyme concentration as a function of fermenter cooler return temperature and enzyme flow.

16. The memory medium of claim 15, wherein said executing the nonlinear control model of yeast growth and fermentable sugar concentration comprises:
executing the nonlinear control model of yeast growth and fermentable sugar concentration as a function of fermentation temperature and starch-converting enzyme concentration using the process information as input, thereby determining values of temperature and starch-converting enzyme concentration for the batch fermentation process that substantially maximize yeast growth and achieve the target fermentable sugar concentration; and
executing the nonlinear control model of temperature and starch-converting enzyme concentration using the process information as input, thereby determining the values for the fermenter cooler return temperature and starch-converting enzyme flow that achieve the determined values of temperature and starch-converting enzyme concentration in the batch fermentation process.

17. The memory medium of claim 11, wherein the batch fermentation process comprises a fed-batch process.

18. The memory medium of claim 11, wherein the batch fermentation process comprises a pure batch process.

19. The memory medium of claim 11, wherein the program instructions are further executable to perform:
performing said receiving process information, said executing the nonlinear control model of yeast growth and fermentable sugar concentration, and said controlling the mash flow rate or the yeast addition rate in an iterative manner to produce the biofuel in a substantially optimal manner.

20. The memory medium of claim 11, wherein the biofuel comprises ethanol, and wherein yeast growth is based on the following equation:

$$\text{yeast growth} = \left( \frac{\mu_x^{max}(T) y_{sugar}}{(k_{x1} + y_{EtOH})(k_{x2} + y_{sugar})} - r_d(t) \right)$$

where $\mu_x^{max}(T)$ is the theoretical maximum yeast growth rate as a function of temperature T, $y_{sugar}$ is the fermentable sugar concentration, $y_{EtOH}$ is an ethanol concentration, $k_{x1}$ is an ethanol saturation constant, $k_{x2}$ is the fermentable sugar saturation constant, and $r_d(T)$ is the yeast death rate as a function of temperature T.

21. A system for managing a batch fermentation process in a biofuel production process, comprising:
a processor; and
a memory medium coupled to the processor, wherein the memory medium stores:
a nonlinear control model of yeast growth and fermentable sugar concentration for biofuel production in a batch fermentation process of a biofuel production process, wherein yeast growth is a function of a cooler return temperature of a fermenter, metabolic heat generation in the fermenter, and a volumetric change in a fermentation tank; and
program instructions, executable by the processor to:
receive process information for the batch fermentation process, wherein the process information includes the fermenter cooler return temperature;
execute the nonlinear control model of yeast growth and fermentable sugar concentration using the process information as input, thereby determining target values of one or more fermentation process variables and an optimal batch temperature trajectory during filling of the fermentation tank that substantially maximizes yeast growth and achieves target fermentable sugar concentrations, wherein the one or more target values comprise a mash flow rate or a yeast addition rate; and
control the mash flow rate or the yeast addition rate during filling of the fermentation tank in accordance with the determined values for the one or more fermentation process variables and the optimal batch temperature trajectory.

22. The system of claim 21, wherein the program instructions are further executable to:
receive an objective function, wherein the objective function specifies the target fermentable sugar concentrations;
wherein said executing the nonlinear control model of yeast growth and fermentable sugar concentration comprises:
an optimizer executing the nonlinear control model of yeast growth and fermentable sugar concentration in an iterative manner to solve the objective function, thereby determining the values for the one or more fermentation process variables.

23. The system of claim 21, wherein the program instructions are further executable to:
perform said receiving process information, said executing the nonlinear control model of yeast growth and fermentable sugar concentration, and said controlling the mash flow rate or the yeast addition rate in an iterative manner to produce the biofuel in a substantially optimal manner.

* * * * *